(12) United States Patent
Zhang et al.

(10) Patent No.: US 12,059,427 B2
(45) Date of Patent: Aug. 13, 2024

(54) TREATMENTS FOR CACHEXIA

(71) Applicant: YINUOKE MEDICINE SCIENCE AND TECHNOLOGY COMPANY LTD., Changchun (CN)

(72) Inventors: Lingbing Zhang, Davis, CA (US); Dongxu Zhang, Changchun (CN)

(*) Notice: Subject to any disclaimer, the term of this patent is extended or adjusted under 35 U.S.C. 154(b) by 0 days.

(21) Appl. No.: 16/961,198

(22) PCT Filed: Jan. 15, 2018

(86) PCT No.: PCT/CN2018/072570
§ 371 (c)(1),
(2) Date: Jul. 9, 2020

(87) PCT Pub. No.: WO2019/136739
PCT Pub. Date: Jul. 18, 2019

(65) Prior Publication Data
US 2021/0052619 A1 Feb. 25, 2021

(51) Int. Cl.
| | | |
|---|---|---|
| *A61K 31/7068* | (2006.01) | |
| *A61K 31/12* | (2006.01) | |
| *A61K 31/192* | (2006.01) | |
| *A61K 31/196* | (2006.01) | |
| *A61K 31/216* | (2006.01) | |
| *A61K 31/40* | (2006.01) | |
| *A61K 31/405* | (2006.01) | |
| *A61K 31/407* | (2006.01) | |
| *A61P 21/06* | (2006.01) | |
| *A61P 35/00* | (2006.01) | |
| *A61P 37/06* | (2006.01) | |

(52) U.S. Cl.
CPC .......... *A61K 31/7068* (2013.01); *A61K 31/12* (2013.01); *A61K 31/192* (2013.01); *A61K 31/196* (2013.01); *A61K 31/216* (2013.01); *A61K 31/40* (2013.01); *A61K 31/405* (2013.01); *A61K 31/407* (2013.01); *A61P 21/06* (2018.01); *A61P 35/00* (2018.01); *A61P 37/06* (2018.01)

(58) Field of Classification Search
CPC ....... A61K 31/7068; A61P 21/06; A61P 37/06
See application file for complete search history.

(56) References Cited

U.S. PATENT DOCUMENTS

2009/0117197 A1* 5/2009 Bascomb ............. A61K 31/138
424/523
2016/0166683 A1* 6/2016 Nunes .................. A61K 31/517
424/278.1

FOREIGN PATENT DOCUMENTS

| CN | 104337828 A | 2/2015 |
|---|---|---|
| CN | 107137417 A | 9/2017 |
| WO | WO 03061626 A1 | 7/2003 |
| WO | WO 2008144880 A1 | 12/2008 |
| WO | WO 2017148129 A1 | 9/2017 |

OTHER PUBLICATIONS

Combined Search and Examination Report under Sections 17 and 18(3) for GB1906991.3 dated Aug. 2, 2019, 7 pages.
Handley, D. A., et al., "Preclinical Enantioselective Pharmacology of (R)- and (S)-Ketorolac," J Clin Pharmacol. Feb. 1998; 38(2S): 25S-35S.
Li, B., "The Study Progress on Clinical Application of Cytarabine," Guangdong Chemical Industry., vol. 41, No. 21, Dec. 31, 2014, pp. 111, 113.
Liu, L. et al., "Progress of Ketorolac Tromethamine Application in Analgesia," Journal of Pediatric Pharmacy, vol. 21, No. 3, Dec. 31, 2015, pp. 60-63.
The International Search Report (ISR) for PCT/CN2018/072570 dated Sep. 30, 2018, 5 pages.
Written Opinion of the International Searching Authority for for PCT/CN2018/072570 dated Sep. 30, 2018, 4 pages.

* cited by examiner

*Primary Examiner* — Pancham Bakshi
(74) *Attorney, Agent, or Firm* — Sandra Poteat Thompson; Finlayson Toffer, LLP

(57) ABSTRACT

Provided are methods and compositions for treating cachexia in order to reduce the morbidity and mortality of chronic illnesses and to improve the effectiveness of treating chronic illness overall. More specifically, provided herein are methods and compositions for treating cachexia by agents that modulate the immune system and/or inflammation.

3 Claims, 8 Drawing Sheets

TREATMENTS FOR CACHEXIA

CROSS-REFERENCE TO RELATED APPLICATIONS

This application is a national stage application under 35 U.S.C. § 371 of International Application No. PCT/CN2018/072570, filed Jan. 15, 2018, the disclosure of which is incorporated by reference herein.

BACKGROUND OF THE INVENTION

Cachexia is a complex metabolic syndrome associated with underlying illness and characterized by loss of muscle with or without loss of fat mass (most commonly manifested as weight loss). It is distinct from starvation, age-related loss of muscle mass, primary depression, malabsorption and hyperthyroidism and is associated with increased morbidity due to illness. About half of all cancer patients show a syndrome of cachexia, contributing to decreased treatment success and survival. Cancer cachectic patients experience complications as varied as reduced chemotherapy effectiveness, mobility, and functionality of muscle systems (e.g. cardiovascular and respiratory systems).

Cachexia remains a largely underestimated and untreated condition. The prevalence of cachexia in cancer patients may reach as high as 86% in the last 1-2 weeks of life, and 45% of cancer patients lose more than 10% of their original body weight over the course of their disease. As death usually occurs once weight loss has reached 30% of the patient's historic body weight, cachexia is a contributing factor in a large number of cancer deaths. To date there is not a single approved treatment for cachexia.

SUMMARY OF THE INVENTION

In view of the foregoing, there is need for methods and compositions for treating cachexia in order to reduce the morbidity and mortality of chronic illnesses and to improve the effectiveness of treating chronic illness overall.

In one aspect, the invention provides a method for treating an immune disorder characterized by (1) increased white blood cell amount, (2) increased neutrophil-to-white-blood-cell ratio, and (3) decreased T-cell-to-white-blood-cell ratio, comprising administering to a subject in need thereof an effective amount of (i) an immunosuppressive agent, (ii) an anti-inflammatory agent, or both. In one aspect, the invention provides a method for treating cachexia, comprising administering to a subject in need thereof an effective amount of an agent selected from the group consisting of (i) an immunosuppressive agent, (ii) an anti-inflammatory agent, or both. In some embodiments, the immune disorder is further characterized by wasting symptoms. In some embodiments, the wasting symptoms comprise fluid-corrected weight loss and at least three or more symptoms selected from the group consisting of decreased muscle strength, fatigue, anorexia, low fat-free mass index, and abnormal biochemistry as exhibited by increased inflammatory markers, anemia, or low serum albumin, and any combination thereof. In some embodiments, the immune disorder is induced by chronic disease. In some embodiments, the chronic disease is selected from the group consisting of AIDS, chronic obstructive pulmonary disease, multiple sclerosis, congestive heart failure, tuberculosis, familial amyloid polyneuropathy, chronic kidney disease, and cystic fibrosis. In some embodiments, the chronic disease is cancer. In some embodiments, the immunosuppressive agent is a pyrimidine nucleoside antimetabolite. In some embodiments, the nucleoside antimetabolite is according to formula I or a pharmaceutically acceptable salt, solvate, hydrate, stereoisomer, or clathrate thereof

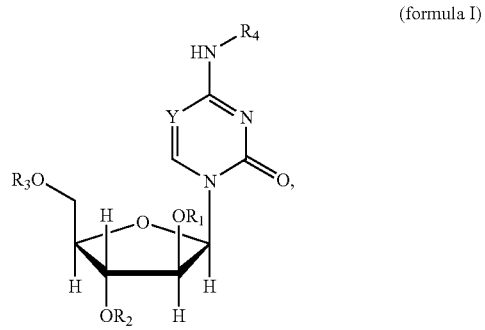

(formula I)

wherein:
Y is N or C;
R1 and R2 are independently selected from the group consisting of hydrogen, aliphatic C2-C5-acyl, benzoyl, and carboxyl-C1-C3-alkylcarbonyl;
R3 is selected from the group consisting of H, aliphatic C1-C24-acyl optionally containing 1-2 double bonds, benzoyl, carboxyl-C1-C3-alkylcarbonyl, phosphate, an alkyl phosphate ester, phorphoramidate, an alkyl phosphoramidate ester, 2,3-dihydroxypropylphosphate, and an acyl ester of 2,3-dihydroxypropylphosphate; and
R4 is selected from the group consisting of H, optionally substituted C1-C24 alkyl optionally containing 1-2 double bonds, optionally substituted aliphatic C1-C24 acyl optionally containing 1-2 double bonds, valyl, leucyl, isoleucyl, asparaginyl, benzoyl, and 4-methoxybenzoyl.

In some embodiments, the pyrimidine nucleoside analog is cytarabine or a pharmaceutically acceptable salt, solvate, hydrate, stereoisomer, clathrate, or prodrug thereof. In some embodiments, the pyrimidine nucleoside analog is cytarabine, cytarabine hydrochloride, valyl cytarabine, Elacytarabine (CP-4055), a cytarabine phosphoramidate, or Astarabine. In some embodiments, the pyrimidine nucleoside analog is cytarabine or cytarabine hydrochloride. In some embodiments, the anti-inflammatory agent is an NSAID. In some embodiments, the NSAID is a nonselective COX inhibitor. In some embodiments, the nonselective COX inhibitor is an acetic acid derivative. In some embodiments, the acetic acid derivative is indomethacin, diclofenac, tolmetin, aceclofenac, sulindac, nabumetone, etodolac, ketorolac, or a pharmaceutically acceptable salt, solvate, hydrate, stereoisomer, clathrate, or prodrug thereof. In some embodiments, the acetic acid derivative is ketorolac or a pharmaceutically acceptable salt, solvate, hydrate, stereoisomer, clathrate, or prodrug thereof. In some embodiments, the acetic acid derivative is a pharmaceutically acceptable salt, solvate, hydrate, stereoisomer, clathrate, or prodrug of ketorolac selected from the group consisting of ketorolac, ketorolac tromethamine, galactosylated ketorolac, a ketorolac alkyl ester, a ketorolac piperazinylalkyl ester, and a ketorolac amide. In some embodiments, the acetic acid derivative is according to formula III or a pharmaceutically acceptable salt, solvate, hydrate, stereoisomer, or clathrate thereof

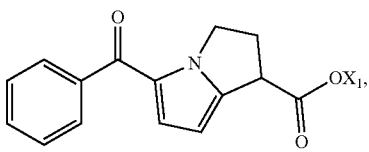
(formula III)

wherein:

X1 is selected from the group consisting of a H, a straight-chain or branched saturated or unsaturated C1-C20 aliphatic group optionally substituted with a C6-C10 aryl group, —NHC6H5, —NHC6H5OCH3, —NHCH2C6H5, —NHCH26H4OCH3, —NHCH2COOCH3, —NHCH2CH2COOC2H5, —NHCH2(CH2)2CH3, —NHC6H10, —NHCH2CH2CH3, —NHCH(CH3)2, —NH(CH2)3OCH3, —NHCH2CH=CH2, optionally substituted talosyl, optionally substituted galactosyl, optionally substituted idosyl, optionally substituted glucosyl, optionally substituted mannosyl, optionally substituted glucosyl, optionally substituted altrosyl, optionally substituted allosyl, optionally substituted alkylpiperidinyl, optionally substituted piperizinyl, optionally substituted alkylpiperazinyl, optionally substituted morpholinyl, and optionally substituted alkylmorpholinyl.

In some embodiments, the acetic acid derivative according to formula III is formula V or a pharmaceutically acceptable salt, solvate, hydrate, or clathrate thereof

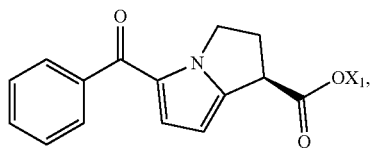
(formula V)

wherein:

X1 is selected from the group consisting of a H, a straight-chain or branched saturated or unsaturated C1-C20 aliphatic group optionally substituted with a C6-C10 aryl group, —NHC6H5, —NHC6H5OCH3, —NHCH2C6H5, —NHCH26H4OCH3, —NHCH2COOCH3, —NHCH2CH2COOC2H5, —NHCH2(CH2)2CH3, —NHC6H10, —NHCH2CH2CH3, —NHCH(CH3)2, —NH(CH2)3OCH3, —NHCH2CH=CH2, optionally substituted talosyl, optionally substituted galactosyl, optionally substituted idosyl, optionally substituted glucosyl, optionally substituted mannosyl, optionally substituted glucosyl, optionally substituted altrosyl, optionally substituted allosyl, optionally substituted alkylpiperidinyl, optionally substituted piperizinyl, optionally substituted alkylpiperazinyl, optionally substituted morpholinyl, and optionally substituted alkylmorpholinyl.

In some embodiments, the acetic acid derivative according to formula V is (R)-ketorolac.

In some embodiments, the method further comprises administering to the subject in need thereof an effective amount of an immunosuppressive agent and an anti-inflammatory agent. In some embodiments, the immunosuppressive agent is according to formula I or a pharmaceutically acceptable salt, solvate, hydrate, stereoisomer, or clathrate thereof and the anti-inflammatory agent is according to formula III or a pharmaceutically acceptable salt, solvate, hydrate, stereoisomer, or clathrate thereof. In some embodiments, the immunosuppressive agent is cytarabine, cytarabine hydrochloride, valyl cytarabine, Elacytarabine (CP-4055), a cytarabine phosphoramidate, or Astarabine and the anti-inflammatory agent is ketorolac, ketorolac tromethamine, galactosylated ketorolac, a ketorolac alkyl ester, a ketorolac piperazinylalkyl ester, or a ketorolac amide. In some embodiments, the immunosuppressive agent is cytarabine or cytarabine hydrochloride and the anti-inflammatory agent is ketorolac or ketorolac tromethamine. In some embodiments, the immunosuppressive agent and the anti-inflammatory agent are administered at a molar ratio of about 20:1 to about 0.8:1. In some embodiments, the immunosuppressive agent and the anti-inflammatory agent are administered in the same composition. In some embodiments, the immunosuppressive agent and the anti-inflammatory agent are administered in separate compositions. In some embodiments, the immunosuppressive agent and the anti-inflammatory agent are administered via separate administration routes. In some embodiments, the immunosuppressive agent and the anti-inflammatory agent are administered within 24 hours of each other. In some embodiments, one or more of the immunosuppressive agent and the anti-inflammatory agent are administered orally. In some embodiments, one or more of the immunosuppressive agent and the anti-inflammatory agent are administered parenterally. In some embodiments, the method:
(a) effectively decreases the white blood cell amount of the subject by at least about 10%;
(b) effectively decreases the neutrophil-to-white-blood-cell ratio of the subject by at least about 10%; and
(c) effectively increases the T-cell-to-white-blood-cell ratio of the subject by at least about 10%. In some embodiments, the method effectively increases the body weight of the subject by at least about 10%.

In one aspect, the invention provides for a composition comprising a therapeutically effective amount of formula I or a pharmaceutically acceptable salt, solvate, hydrate, stereoisomer, or clathrate thereof and the anti-inflammatory agent is according to formula III or a pharmaceutically acceptable salt, solvate, hydrate, stereoisomer, or clathrate thereof. In some embodiments, the anti-inflammatory agent according to formula III is according to formula V or a pharmaceutically acceptable salt, solvate, hydrate, stereoisomer, or clathrate thereof. In some embodiments, the anti-inflammatory agent according to formula V is (R)-ketorolac. In some embodiments, the immunosuppressive agent and the anti-inflammatory agent are present in the composition at a molar ratio of about 20:1 to about 0.8:1. In some embodiments, the immunosuppressive agent is cytarabine, cytarabine hydrochloride, valyl cytarabine, elacytarabine (CP-4055), a cytarabine phosphoramidate, or Astarabine and the anti-inflammatory agent is ketorolac, ketorolac tromethamine, galactosylated ketorolac, a ketorolac alkyl ester, a ketorolac piperazinylalkyl ester, or a ketorolac amide. In some embodiments, the immunosuppressive agent is cytarabine or cytarabine hydrochloride and the anti-inflammatory agent is ketorolac or ketorolac tromethamine. In some embodiments, the composition further comprises a therapeutically acceptable excipient. In some embodiments, the composition is formulated for oral administration. In some embodiments, the composition is formulated for parenteral administration.

In one aspect, the invention provides a kit containing a first dosage form comprising a therapeutically effective dose of an immunosuppressant agent according to formula I or a pharmaceutically acceptable salt, solvate, hydrate, stereoisomer, or clathrate thereof and a second dosage form comprising a therapeutically effective dose of an anti-inflammatory agent according to formula III or a pharmaceutically acceptable salt, solvate, hydrate, stereoisomer, or clathrate thereof. In some embodiments, the anti-inflammatory agent according to formula III is according to formula V or a pharmaceutically acceptable salt, solvate, hydrate, stereoisomer, or clathrate thereof. In some embodiments, the anti-inflammatory agent according to formula V is (R)-ketorolac. In some embodiments, the immunosuppressive agent is cytarabine, cytarabine hydrochloride, valyl cytarabine, elacytarabine (CP-4055), a cytarabine phosphoramidate, or Astarabine and the anti-inflammatory agent is ketorolac, ketorolac tromethamine, galactosylated ketorolac, a ketorolac alkyl ester, a ketorolac piperazinylalkyl ester, or a ketorolac amide. In some embodiments, the immunosuppressive agent is cytarabine, cytarabine hydrochloride and the anti-inflammatory agent is ketorolac or ketorolac tromethamine. In some embodiments, the dose ratio of the immunosuppressive agent and the anti-inflammatory agent in the kit is about 20:1 to about 0.8:1. In some embodiments, the first or second dosage form is oral. In some embodiments, the first or second dosage form is parenteral.

In one aspect, the invention provides for a method for treating a subject suffering from a primary condition accompanying cachexia, comprising alternatively administering to the subject in need thereof: (i) an effective amount of an immunosuppressive agent according to formula I or a pharmaceutically acceptable salt, solvate, hydrate, stereoisomer, or clathrate thereof and an effective amount of an anti-inflammatory agent according to formula III or a pharmaceutically acceptable salt, solvate, hydrate, stereoisomer, or clathrate thereof; and (ii) an additional agent in an effective amount for treating the primary condition, wherein the primary condition is cancer. In some embodiments, the immunosuppressive agent is cytarabine or cytarabine hydrochloride and the anti-inflammatory agent is ketorolac or ketorolac tromethamine. In some embodiments, the anti-inflammatory agent according to formula III is formula V or a pharmaceutically acceptable salt, solvate, hydrate, stereoisomer, or clathrate thereof. In some embodiments, the anti-inflammatory agent according to formula V is (R)-ketorolac. In some embodiments, the immunosuppressive agent and the anti-inflammatory agent are administered within 24 hours of each other. In some embodiments, (i) and (ii) are separated by a non-treatment interval of at least 1 week.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 5 is a Kaplan-Meier survival curve of mice treated for 3 treatment cycles with 3:1, 6:1 and 9:1 ratios of Cytarabine to Ketorolac.

FIG. 6 shows that recovery of these parameters was achieved after the combination therapy.

DETAILED DESCRIPTION OF THE INVENTION

I. Definitions

Figure 1:
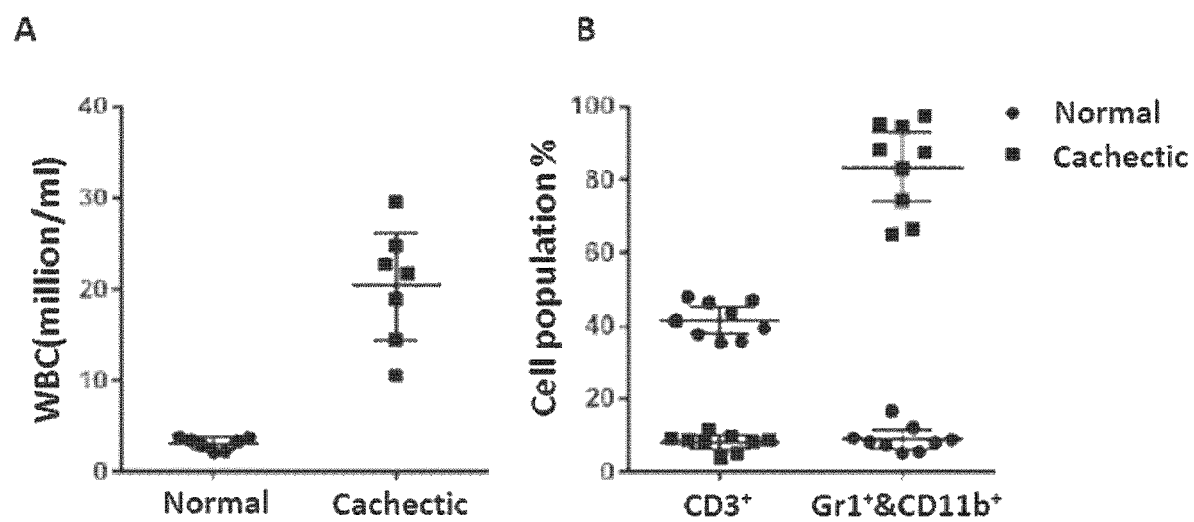
FIG. 1 demonstrates that mice under cachexia have a significantly elevated total white blood cell count accounted for by increased Gr1+/CD11b+ neutrophils and decreased CD3+ lymphocytes; (A) is a graph depicting number of total white blood cells in cachectic versus naïve Balb/c mice, and (B) is a graph depicting ratios of CD3+ lymphocytes and Gr1+/CD11b+ neutrophils to total white blood cells in naïve versus cachectic Balb/c mice.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

The terms "treat," "treating" or "treatment," as used herein, may include alleviating, abating or ameliorating a disease or condition symptoms, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

The term "primary disease" or "primary disease accompanying cachexia" refers to a disease known in the medical literature associated with cachexia; in some embodiments a primary disease accompanying cachexia is chronic/severe organ dysfunction (e.g. congestive heart failure), a chronic infectious disease (e.g. AIDS), an autoimmune disease (e.g. Crohn's disease), or cancer. As used herein, the term "treating a primary disease accompanying cachexia" does not necessarily involve regression of the primary disease, but rather treatment of cachexia in a way to facilitate treatment of the primary disease.

The term "therapeutically effective amount" or "effective amount" may generally refer to the amount (or dose) of a compound or other therapy that is minimally sufficient to prevent, reduce, treat or eliminate a condition, or risk thereof, when administered to a subject in need of such compound or other therapy. In some instances the term "therapeutically effective amount" may refer to that amount of compound or other therapy that is sufficient to have a prophylactic effect when administered to a subject. The therapeutically effective amount may vary; for example, it may vary depending upon the subject's condition, the weight and age of the subject, the severity of the disease condition, the manner of administration and the like, all of which may be determined according to standard pharmacodynamic dosing models. The amount of the compound actually administered may be determined by a physician or caregiver, in the light of the relevant circumstances, including the condition to be treated, the chosen route of administration, the compound administered and its relative activity, the age, weight, the response of the individual patient, the severity of the patient's symptoms, and the like.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "prodrug" is meant to indicate a compound that may be converted under physiological conditions or by solvolysis to a biologically active compound described herein. Thus, the term "prodrug" refers to a precursor of a biologically active compound that is pharmaceutically acceptable. In some aspects, a prodrug is inactive when administered to a subject but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam); Higuchi, T., et al., "Pro-drugs as Novel Delivery Systems," (1987) A.C.S. Symposium Series, Vol. 14; and Bioreversible Carriers in Drug Design, ed. Edward B. Roche, American Pharmaceutical Association and Pergamon Press) each of which is incorporated in full by reference herein for the purposes of describing how compounds may be modified with prodrug moieties. The term "prodrug" is also meant to include any covalently bonded carriers, which release the active compound in vivo when such prodrug is administered to a mammalian subject. Prodrugs of an active compound, as described herein, are typically prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of a hydroxy functional group, or acetamide, formamide and benzamide derivatives of an amine functional group in the active compound and the like.

The term "salt" or "pharmaceutically acceptable salt" refers to salts derived from a variety of organic and inorganic counter ions well known in the art. Salts include, for example, acid-addition salts and base-addition salts. The acid that is added to a compound to form an acid-addition salt can be an organic acid or an inorganic acid. Inorganic acids from which salts can be derived include, for example, hydrochloric acid, hydrobromic acid, sulfuric acid, nitric acid, iodic acid, phosphoric acid, carbonic acid, and the like. Organic acids from which salts can be derived include, for example, acetic acid, propionic acid, glycolic acid, pyruvic acid, oxalic acid, maleic acid, malonic acid, malic acid, succinic acid, fumaric acid, tartaric acid, bitartaric acid, citric acid, benzoic acid, cinnamic acid, mandelic acid, methanesulfonic acid, methylsulfonic acid, naphthalenesulfonic acid, camphorsulfonic acid, ethanedisulfonic acid, laurylsulfuric acid, ethanesulfonic acid, p-toluenesulfonic acid, pamoic acid, glucoheptonic acid, gluconic acid, glucuronic acid, hippuric acid, isethionic acid, lactic acid, lactobionic acid, salicylic acid, stearic acid, toluenesulfonic acid, phenylsulfonic acid, and the like. A base that is added to a compound to form a base-addition salt can be an organic base or an inorganic base. In some cases, a salt can be a metal salt. In some cases, a salt can be an ammonium salt. Inorganic bases from which salts can be derived include, for example, sodium, potassium, lithium, ammonium, calcium, diolamine, lysine, meglumine, magnesium, oleamine, tromethamine, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like.

The term "solvate" means a compound of the present invention or a salt thereof, which further includes a stoichiometric or non-stoichiometric amount of pharmaceutically-acceptable solvent bound by non-covalent intermolecular forces. Where the solvent is water, the solvate is a hydrate.

The term "clathrate" means a compound of the present invention or a salt thereof in the form of a crystal lattice that contains spaces (e.g., channels) that have a guest molecule (e.g., a pharmaceutically-acceptable solvent or water) trapped within.

The term "stereoisomer" refers to a compound made up of the same atoms bonded by the same bonds but having different three-dimensional structures, which are not interchangeable. The present disclosure contemplates various stereoisomers and mixtures thereof and includes "enantiomers," which refers to two stereoisomers whose molecules are nonsuperimposable mirror images of one another. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers.

The term "cachexia" refers to a complex metabolic syndrome associated with underlying illness and characterized by loss of muscle with or without loss of fat mass. The prominent clinical feature of cachexia is fluid-retention-corrected weight loss in adults or non-endocrine growth failure in children. Anorexia, inflammation, insulin resistance and increased muscle protein breakdown are frequently associated with cachexia. Cachexia is distinct from starvation, age-related loss of muscle mass, primary depression, malabsorption and hyperthyroidism and is associated with increased morbidity. For cachexia caused by cancer (e.g. tumors or cancer of specific tissue types) in humans, the agreed diagnostic criterion (see e.g. Fearon et al. Lancet Oncol 2011; 12: 489-95, which provides diagnostic criteria for cachexia and its staging) is weight loss greater than 5%, or weight loss greater than 2% in individuals already showing depletion according to current bodyweight and height (body-mass index [BMI]<20 kg/m$^2$) or skeletal muscle mass (sarcopenia).

The term "white blood cell" or "leukocyte" refers to a nucleated circulating cell of hematopoietic origin involved in protecting the body against both infectious disease and foreign invaders. The term "white blood cell" encompasses various subtypes of cells with distinct immune functions including but not limited to granulocytes, monocytes, and lymphocytes. The population of white blood cells in blood samples from a subject can be determined by a variety of methods including direct manual or automated (e.g. with a device such as Coulter S-Plus Jr) counting of whole diluted blood on a hemocytometer, white blood cell isolation by centrifugation followed by manual or automated counting, or resuspension of blood in a red blood cell lysis buffer followed by manual or automated counting. In some embodiments, white blood cells are measured in terms of an absolute cell count (e.g. number of cells per volume blood).

The term "T-cell" refers to a subset of white blood cell (e.g. lymphocyte) that plays a central role in cell-mediated immunity. T-cells are distinguished from other lymphocytes (e.g. B-cells) by the presence of a T-cell receptor, a molecule responsible for recognizing fragments of antigen as peptides bound to major histocompatibility complex (MHC) molecules, on their surface. An exemplary method of distinguishing T-cells via immunoreactive methods (e.g. immunofluorescence, IHC, FACS) involves assaying for the presence of the CD3 co-receptor on their surface. The term "T-cell" encompasses various subtypes of cells with distinct immunological functions, including but not limited to helper T-cells, cytotoxic T-cells, memory T-cells, T regulatory cells, natural killer T-cells, mucosal associated invariant T-cells, and gamma delta T-cells. In measurements of T-cells, T-cells may be represented as an absolute (e.g. cell count per volume blood) or relative population size (e.g. pre-treatment to post treatment), as a fraction of total white blood cells, or ratiometrically with respect to a larger genus encompassing the given cell (e.g. T-cell to white blood cell ratio, or percentage of white blood cells that are T-cells).

The term "neutrophil" refers to a subset of highly motile white blood cell (e.g. granulocyte) which is specialized for the uptake of particulate material by phagocytosis and is capable of entering tissues that become infected or inflamed. Neutrophils may be sub-classified into types such as high-density neutrophils and low-density neutrophils. Like T-cells, neutrophils can be distinguished from other white blood cells by assaying by immunoreactive methods (e.g. immunofluorescence, IHC, FACS) molecules present on their surface; however, the markers used differ between human and mouse. In mouse, neutrophils can be distinguished, for example, by the presence of cell surface markers such as CD11b, Ly6G, and Gr1. In human, neutrophils can be distinguished, for example, by the presence of cell surface markers such as CD15 and CD16 and the absence of cell surface markers such as CD49d. In measurements of neutrophils, neutrophils may be represented as an absolute (e.g. cell count per volume blood) or relative population size (e.g. pre-treatment to post treatment), as a fraction of total white blood cells, or ratiometrically with respect to a larger genus encompassing the given cell (e.g. neutrophil to white blood cell ratio, or percentage of white blood cells that are neutrophils).

The term "immunosuppressive agents" refers to drugs that inhibit or prevent activity of the immune system. Immunosuppressive agents include, but are not limited to, classes such as cytostatics (e.g. alkylating agents, antimetabolites), drugs acting on immunophilins (e.g. ciclosporin, tacrolimus, sirolimus), anti-lymphocyte antibodies, opioids, TNF-binding agents, mycophenolates, and sphingosine-targeted agents (e.g. myriocin and fingolimod).

The term "anti-inflammatory agents" refers to drugs that reduce inflammation or swelling. Anti-inflammatory agents include, but are not limited to, classes such as NSAIDs (e.g. COX inhibitors such as aspirin and ibuprofen), steroidal anti-inflammatory drugs (e.g. corticosteroids), and antileukotrienes.

The term "NSAID" refers a nonsteroidal anti-inflammatory agent. NSAIDs are known for their inhibition of cyclooxygenases I and II (the enzymes responsible for the biosynthesis of the prostaglandins and certain related autacoids). NSAIDs are known to be antipyretic, analgesic, and anti-inflammatory. Exemplary NSAIDs can be found in, e.g. The Pharmacological Basis of Therapeutics, 9th edition, Macmillan Publishing Co., 1996, pp 617-655.

II. Overview

The present disclosure describes a method of treating subjects suffering from a condition characterized by an immune disorder comprising one or more of the following: (1) increased white blood cell count, (2) increased neutrophil-to-white-blood-cell ratio, and (3) decreased T-cell-to-white-blood-cell ratio using (a) an immunosuppressive agent or agents, (b) an anti-inflammatory agent or agents, or (c) a combination of immunosuppressive and anti-inflammatory agents. In cases where a combination of immunosuppressive and anti-inflammatory agents is administered, the immunosuppressive and anti-inflammatory agents may be administered simultaneously, separately, or sequentially. Treatment of this underlying immune disorder provides, in some embodiments, a more direct and effective route of treating conditions considered to result from it such as cachexia (and especially cancer cachexia).

This disclosure also describes a method of treating a subject suffering from a primary condition accompanying cachexia using an effective amount of an (i) an immunosuppressive agent, (ii) an anti-inflammatory agent, or both; in combination with an effective amount of an agent for treating the primary condition. Treatment of cachexia alongside the primary condition enables, in some embodiments, treatment of the primary condition with fewer treatment interruptions, side effects, and/or adverse consequences.

This disclosure further provides compositions comprising one or more of an immune suppressive agent and an anti-inflammatory agent. In some cases, the composition further comprises a pharmaceutically-acceptable excipient.

III. Subjects to be Treated

The subjects treated by the methods and compositions provided herein may have or may be suspected of having any of a number of chronic progressive diseases. The methods and compositions herein may thus include methods or compositions for treating a subject suffering or suspected to be suffering from a chronic and/or progressive disease. Many chronic and/or progressive diseases are also accompanied by wasting syndromes, such as cachexia. The methods and compositions herein may thus include methods of treating subjects suffering from chronic and/or progressive diseases accompanied by a wasting syndrome, such as cachexia (see e.g. Evans et al. Clinical Nutrition (2008) 27, 793-799, which outlines broad features and disease associations of cachexia).

The subjects are preferably human subjects or patients, but in some cases may be non-human subjects, (e.g., non-human mammals). Examples of non-human mammals include, but are not limited to, non-human primates (e.g., apes, monkeys, and gorillas), rodents (e.g., mice, rats), cows, pigs, sheep, horses, dogs, cats, and rabbits.

The co-occurrence of cachexia alongside chronic and/or progressive diseases poses significant complications to their treatment, as the skeletal muscle dysfunction/skeletal muscle loss places patients at increased risk of morbidity and mortality even with refeeding and parenteral nutrition.

A major class of chronic and/or progressive diseases associated with cachexia is diseases or conditions involving severe organ dysfunction. Thus, in some cases, subjects treated according to methods herein have chronic obstructive pulmonary disease, congestive heart failure, chronic kidney disease, cystic fibrosis, or have suffered trauma. In some embodiments subjects have chronic obstructive pulmonary disease. In some embodiments, subjects have congestive heart failure. In some embodiments, subjects have chronic kidney disease. In some embodiments, subjects have cystic fibrosis. In some embodiments, subjects have suffered trauma.

Another major class or chronic and/or progressive diseases associated with cachexia are diseases with infectious etiology. In some cases, subjects treated according to methods herein have AIDS, sepsis, chronic infection, or tuberculosis. In some embodiments, subjects have AIDS. In some embodiments, subjects suffer from sepsis. In some embodiments, subjects suffer from chronic infection. In some embodiments subjects have tuberculosis.

Other types of diseases associated with cachexia include autoimmune disease (e.g. multiple sclerosis, rheumatoid arthritis, Crohn's disease), amyloid diseases (e.g. familiar amyloid polyneuropathy), and Type I diabetes. In some embodiments, subjects treated using methods or compositions described herein have an autoimmune disease, an amyloid disease, or type I diabetes. In some embodiments, subjects have multiple sclerosis. In some embodiments, subjects have rheumatoid arthritis. In some embodiments, subjects have Crohn's disease. In some embodiments, subjects have familial amyloid polyneuropathy. In some embodiments, subjects have Type I diabetes.

A major class of chronic progressive diseases associated with cachexia is tumorigenic conditions such as cancer. Cancer is a collection of related diseases characterized by uncontrolled proliferation of cells with the potential to metastasize throughout the body. Cancer can be classified into five broad categories including, for example, carcinomas, sarcomas, lymphomas, leukemias, and adenomas. Carcinomas can arise from cells that cover internal and external parts of the body such as the lung, breast, and colon. Sarcomas can arise from cells that are located in bone, cartilage, fat, connective tissue, muscle, and other supportive tissues. Lymphomas can arise in the lymph nodes and immune system tissues. Leukemias can arise in the bone marrow and accumulate in the bloodstream. Adenomas can arise in the thyroid, the pituitary gland, the adrenal gland, and other glandular tissues.

In some embodiments, subjects have or are suspected of having cancer or a tumorigenic syndrome. Cancer may include thymus, brain, lung, skin, eye, oropharyngeal, gastrointestinal, pancreatic, breast, head, neck, renal, liver, ovarian, testicular, gynecological, thyroid, AIDS-related cancer, or Viral induced cancer. Tumorigenic conditions also include tumors (e.g. of the cancer types described previously), a CNS tumor, and paraneoplastic neurologic syndrome. In some embodiments, cancer is thymus cancer. In some embodiments, cancer is brain cancer (e.g. gliomas, meningiomas). In some embodiments, cancer is lung cancer (e.g. lung adenocarcinoma). In some embodiments, cancer is skin cancer (e.g. squamous cell carcinoma). In some embodiments, cancer is eye cancer (e.g. retinoblastoma, intraocular melanoma). In some embodiments cancer is oral cavity or oropharyngeal cancer. In some embodiments, cancer is bladder cancer. In some embodiments, cancer is gastric cancer. In some embodiments, cancer is pancreatic cancer. In some embodiments, cancer is a gynecological cancer (e.g. cervical cancer, ovarian cancer). In some embodiments, cancer is head or neck cancer. In some embodiments, cancer is renal cancer. In some embodiments cancer is prostate cancer. In some embodiments, cancer is testicular cancer. In some embodiments, cancer is AIDS-related cancer (e.g. Kaposi's sarcoma). In some embodiments, cancer is Viral-induced cancer (e.g. Burkitt's lymphoma, nasopharyngeal carcinoma caused by EBV). In some embodiments, the tumorigenic syndrome is a CNS tumor. In some embodiments, the tumorigenic condition is paraneoplastic neurologic syndrome.

Other non-limiting examples of cancer that can be treated by compositions or methods according to the invention include: acute lymphoblastic leukemia, acute myeloid leukemia, adrenocortical carcinoma, AIDS-related cancers, AIDS-related lymphoma, anal cancer, appendix cancer, astrocytomas, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenström macroglobulinemia, and Wilms tumor.

Subjects in need of treatment according to the methods and compositions provided herein may be male or female. Subjects may include adults, teenagers, adolescents, children, toddlers, infants, and neonates. Such subjects may be of a range of ages, which may include >10 minutes old, >1 hour old, >1 day old, >1 month old, >2 months old, >6 months old, >1 year old, >2 years old, >5 years old, >10 years old, >15 years old, >18 years old, >25 years old, >35 years old, >45 years old, >55 years old, >65 years old, >80 years old, <80 years old, <70 years old, <60 years old, <50 years old, <40 years old, <30 years old, <20 years old or <10 years old. Subjects may have differing genetic backgrounds, including different racial groups or genetically admixed populations.

IV. Therapeutic Agents

The methods provided herein include administering a therapeutic agent (e.g. anti-inflammatory agent, immunosuppressive agent, or combination of an anti-inflammatory agent and immunosuppressive agent) to a subject.

In some embodiments, the methods or compositions provided herein involve the administration or inclusion of an immunosuppressive agent alone or in combination with an anti-inflammatory agent. Immunosuppressive agents include several classes of agents that work by differing mechanisms including but not limited to cytostatics, drugs acting on immunophilins (e.g. cyclosporin, rapamycin, sirolimus), antibodies targeting immune cells (e.g. anti-lymphocyte antibodies, anti-thymocyte globulin, anti-lymphocyte globulin, anti-neutrophils, etc.), opioids (e.g. fentanyl), TNF-binding agents (e.g. TNF-receptor analogs and anti-TNFalpha antibodies), mycophenolates (e.g. Mycophenolic acid and mycophenolate mofetil), and sphingosine-targeted agents (e.g. Myriocin and Fingolimod). In some embodiments, the methods and compositions disclosed herein include the use of immunosuppressive agents selected from the group consisting of cytostatics, drugs acting on immunophilins, anti-lymphocyte antibodies, opioids, TNF-binding agents, mycophenolates, and sphingosine-targeted agents, and any combination thereof.

Cytostatics are agents that prevent cell division, and thus inhibit immune activity by affecting the proliferation of immune cells (e.g. Neutrophils, T-cells or B-cells). Cytostatics can be grouped into two major classes: alkylating agents and antimetabolites. In some embodiments the methods and compositions disclosed herein include the use of immunosuppressive agents selected from the group consisting of alkylating agents and antimetabolites, and any combination thereof. In some embodiments, the methods and compositions disclosed herein include the use of cytostatics that target proliferation of Neutrophils, T-cells, B-cells, or both (e.g. lymphocyte-suppressing agents, leukocyte-suppressing agents).

Alkylating agents are reactive immunosuppressive agents that attach an alkyl group to DNA, and thereby interfere with cell proliferation (e.g. of immune cells). The DNA alkylation characteristic of alkylating agents can be accompanied by a wide variety of structurally different moieties, including nitrogen/sulfur mustards, nitrosoureas, and organoplatinum compounds. In some embodiments, the methods and compositions disclosed herein include the use of immunosuppressant agents selected from the group consisting of nitrogen/sulfur mustards, nitrosoureas, and organoplatinum compounds, and any combination thereof. Nitrogen/sulfur mustards include, for example, Mechlorethamine, Cyclophosphamide, Chlorambucil, Melphalan, and Ifosfamide. Nitrosoureas include, for example, Carmustine, Lomustine, Arabinopyranosyl-N-methyl-N-nitrosourea, Chlorozotocin, Ethylnitrosourea, Fotemustine, Lomustine, Nimustine, N-Nitroso-N-methylurea, Ranimustine, Semustine, and Streptozocin, and any pharmaceutically acceptable salt, solvate, hydrate, stereoisomer, clathrate, and prodrug thereof and are notable because they are able to penetrate the blood brain barrier. Organoplatinum compounds include, for example, Oxaliplatin, Carboplatin, Cisplatin, and Nedaplatin and any pharmaceutically acceptable salt, solvate, hydrate, stereoisomer, clathrate, and prodrug thereof.

Antimetabolites are immunosuppressive agents that interfere with the synthesis of nucleic acids, and thereby interfere with cell proliferation (e.g. of immune cells). Antimetabolites include several classes of drugs with different structures and modes of action, including but not limited to antifolates and nucleotide analogs (purine analogs and pyrimidine analogs). In some embodiments, the methods and compositions disclosed herein include the use of immunosuppressant agents selected from the group consisting of antifolates, nucleotide analogs, purine analogs, and pyrimidine analogs, and any combination thereof. Antifolates counteract the use or actions of folic acid (vitamin B9) in cells, and thereby inhibit methyltransferases involved in serine, methionine, thymidine and purine biosynthesis that are important for nucleic acid synthesis. Antifolates include compounds such as Methotrexate and Pemetrexed and any pharmaceutically acceptable salt, solvate, hydrate, stereoisomer, clathrate, and prodrug thereof. Purine analogs are compounds with structural similarity to purine nitrogenous bases that may interfere with nucleic acid synthesis by competition with endogenous purine bases and/or may retro-inhibit enzymes responsible of the synthesis of purine nucleotides in the cell. Purine analogs include, but are not limited to Fludarabine, Pentostatin, Cladribine, Azathioprine, and Mercaptopurine and any pharmaceutically acceptable salt, solvate, hydrate, stereoisomer, clathrate, and prodrug thereof. In some embodiments, the methods and compositions disclosed herein include the use of immunosuppressant agents selected from the group consisting of Fludarabine, Pentostatin, Cladribine, Azathioprine, and Mercaptopurine, and any pharmaceutically acceptable salt, solvate, hydrate, stereoisomer, clathrate, and prodrug thereof. Pyrimidine analogs are compounds with structural similarity to pyrimidine nitrogenous basis that may interfere with nucleic acid synthesis by competition with endogenous pyrimidine bases and/or may retro-inhibit enzymes responsible of the synthesis of pyrimidine nucleotides in the cell. Pyrimidine analogs include, but are not limited to, Cytarabine, 5-Fluorouracil, 5-fluorodeoxyuridine, Gemcitabine, Capecitabine, Tegafur-uracil, Azacitidine, and Decitabine and any pharmaceutically acceptable salt, solvate, hydrate, stereoisomer, clathrate, and prodrug thereof (e.g. the free acid of cytarabine or a salt of cytarabine such as cytarabine hydrochloride). In some embodiments, the methods and compositions disclosed herein include the use of immunosuppressant agents selected from the group consisting of Cytarabine, 5-Fluorouracil, 5-fluorodeoxyuridine, Gemcitabine, Capecitabine, Tegafur-uracil, Azacitidine, and Decitabine and any combination thereof, including any pharmaceutically acceptable salt, solvate, hydrate, stereoisomer, clathrate, and prodrug thereof. Cytarabine, in particular, encompasses a number of named pharmaceutically-acceptable forms for administration, which may be used in methods or compositions according to the invention described herein, including Cytarabine, Cytarabine-HCl, L-valyl-ara-C (valyl cytarabine), Elacytarabine (CP-4055), CNDAC ((1-(2-C-cyano-2-deoxybeta-d-arabino-pentofuranosyl) cytosine), Sapacitabine, Cytarabine phosphoramidate prodrugs (see e.g. Tobias et al. Molecular Pharmaceutics, 2004, 1 (2), pp 112-116), and Astaracitabine. In some embodiments, the methods and compositions disclosed herein include the use of immunosuppressant agents selected from the group consisting of Cytarabine-HCl, L-valyl-ara-C (valyl cytarabine), Elacytarabine (CP-4055), CNDAC ((1-(2-C-cyano-2-deoxybeta-d-arabino-pentofuranosyl) cytosine), Sapacitabine, Cytarabine phosphoramidite prodrugs (see e.g. Tobias et al. Molecular Pharmaceutics, 2004, 1 (2), pp 112-116), Fostebine, Cytarabine ocfosfate hydrate, Palmitoyl cytarabine, Adamantyl cytarabine, Enocitabine, and Astaracitabine, and any combination thereof.

In some embodiments, the methods provided herein involve the administration or use of an immunosuppressant agent (e.g. cytarabine derivative) according to formula I or a pharmaceutically acceptable salt, solvate, hydrate, stereoisomer, or clathrate thereof

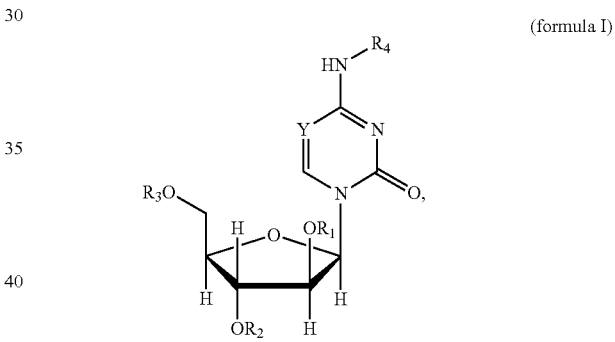

(formula I)

wherein:

Y is N or C;

R1 and R2 are independently selected from the group consisting of hydrogen, aliphatic C2-C5-acyl, benzoyl, and carboxyl-C1-C3-alkylcarbonyl;

R3 is selected from the group consisting of H, aliphatic C1-C24-acyl optionally containing 1-2 double bonds, benzoyl, carboxyl-C1-C3-alkylcarbonyl, phosphate, an alkyl phosphate ester, phorphoramidate, an alkyl phosphoramidate ester, 2,3-dihydroxypropylphosphate, and an acyl ester of 2,3-dihydroxypropylphosphate; and R4 is selected from the group consisting of H, optionally substituted C1-C24 alkyl optionally containing 1-2 double bonds, optionally substituted aliphatic C1-C24 acyl optionally containing 1-2 double bonds, valyl, leucyl, isoleucyl, asparaginyl, benzoyl, and 4-methoxybenzoyl.

In some embodiments, the anti-inflammatory agent according to formula I or a pharmaceutically acceptable salt, solvate, hydrate, stereoisomer, or clathrate thereof is according to formula II:

(formula II)

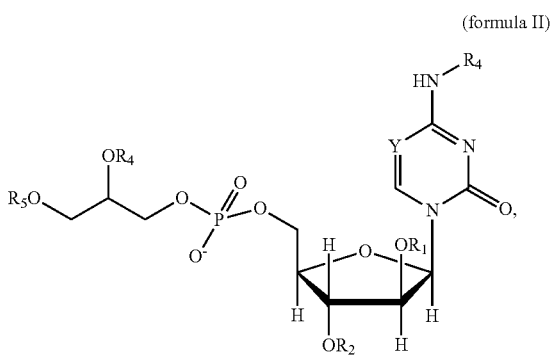

wherein:

R4 and R5 are independently selected from H, aliphatic C1-C24-acyl optionally containing 1 to 2 double bonds, and branched aliphatic C1-C24-acyl optionally containing 1 to 2 double bonds.

Examples of synthesis, chemical structure, and properties of other cytarabine analogs or related compounds can be found, e.g., in U.S. Pat. Nos. 5,641,758A, 6,316,425 B1, Tobias et al. Molecular Pharmaceutics, 2004, 1 (2), pp 112-116, and Cheon et al. Acta Pharmacol Sin. 2007 February; 28(2):268-72, In some embodiments, the immunosuppressant agent is one of the compounds provided in Table 1, or a pharmaceutically acceptable salt, solvate, hydrate, stereoisomer, or clathrate thereof:

TABLE 1

Exemplary Cytarabine-Related Compounds

| Name | Alternate Name | Chemical Structure |
|---|---|---|
| Cytarabine (free base) | 1-(β-D-Arabinofuranosyl)cytosine; Ara-C | 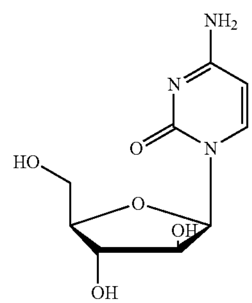 |
| Valyl cytarabine | L-valyl-ara-C | 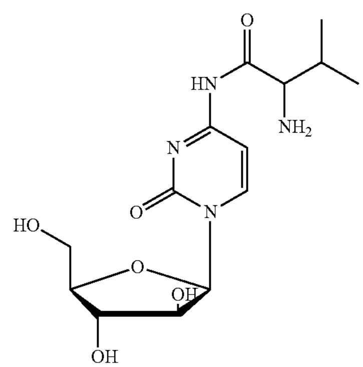 |
| Elacytarabine | CP-4055; [(2R,3S,4S,5R)-5-(4-amino-2-oxopyrimidin-1-yl)-3,4-dihydroxyoxolan-2-yl]methyl (E)-octadec-9-enoate | 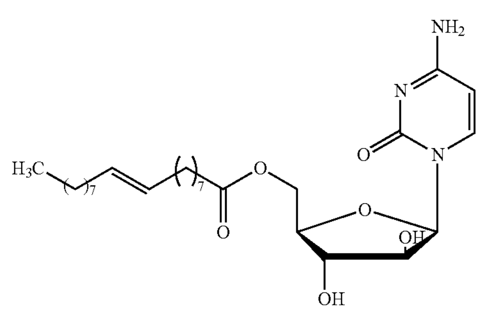 |

TABLE 1-continued

Exemplary Cytarabine-Related Compounds

| Name | Alternate Name | Chemical Structure |
| --- | --- | --- |
| Astarabine | BST-236 | (structure shown) |

In some embodiments, the methods provided herein involve the administration or use of an anti-inflammatory agent alone or in combination with an immunosuppressant. Anti-inflammatory agents include drugs that reduce inflammation or swelling. Anti-inflammatory agents include, but are not limited to, classes such as steroidal anti-inflammatory drugs, NSAIDs, and antileukotrienes. In some embodiments, the methods and compositions disclosed herein include the use of anti-inflammatory agents selected from the group consisting of steroidal anti-inflammatory drugs, NSAIDs, and antileukotrienes, and any combination thereof.

Steroidal anti-inflammatory drugs (e.g. corticosteroids) are analogs of natural steroid hormones such as cortisol that interact with the glucocorticoid receptor, which alters gene transcription to either induce (transactivate) or repress (transrepress) gene transcription in both inflammatory leukocytes and in structural cells, such as epithelium, thus inhibiting inflammation. In some embodiments, the methods and compositions disclosed herein include the use of corticosteroids. A number of synthetic corticosteroids are available that are suitable for administration to subjects, such as prednisone, prednisolone, dexamethasone, betamethasone, methylprednisolone, triamcinolone, hydrocortisone, and cortisone.

NSAIDs (non-steroidal anti-inflammatory drugs) are drugs that exhibit antipyretic, analgesic, and anti-inflammatory effects through their inhibition of cyclooxygenase (COX) enzymes I and II. NSAIDs are classified by both their chemical structural features and their COX I/11 selectivity; exemplary classes of NSAIDs that may be used in methods and compositions disclosed herein include Salicylates, Propionic acid derivatives, Acetic acid derivatives, Enolic acid (Oxicam) derivatives, Anthranilic acid (Fenamate) derivatives, Selective COX-2 inhibitors, Nonselective COX inhibitors, and Sulfonanilides. As all NSAIDs incorporate chiral centers, NSAIDs as described herein specifically include both racemates and enantiomerically pure forms. Salicylates are derivatives of salicylic acid; exemplary salicylates that may be used in methods and compositions disclosed herein include, but are not limited to, Aspirin (acetylsalicylic acid), Diflunisal (Dolobid), Salicylic acid, and Salsalate (Disalcid), and any pharmaceutically acceptable salt, solvate, hydrate, stereoisomer, clathrate, and prodrug thereof. Propionic acid derivatives are aromatic derivatives of propionic acid; exemplary NSAID propionic acid derivatives that may be used in methods and compositions disclosed herein include, but are not limited to, Ibuprofen, Dexibuprofen, Naproxen, Fenoprofen, Ketoprofen, Dexketoprofen, Flurbiprofen, Oxaprozin, and Loxoprofen, and any pharmaceutically acceptable salt, solvate, hydrate, stereoisomer, clathrate, and prodrug thereof. Acetic acid derivatives are aromatic derivatives of acetic acid; exemplary NSAID acetic acid derivatives that may be used in methods and compositions disclosed herein include, but are not limited to, Indomethacin, Tolmetin, Sulindac, Etodolac, Ketorolac, Diclofenac, Aceclofenac, and Nabumetone, and any pharmaceutically acceptable salt, solvate, hydrate, stereoisomer, clathrate, and prodrug thereof (e.g. ketorolac, or a salt form of ketorolac such as ketorolac tromethamine). Enolic acid NSAID derivatives that may be used in methods and compositions disclosed herein include, but are not limited to, Piroxicam, Meloxicam, Tenoxicam, Droxicam, Lornoxicam, and Isoxicam, and any pharmaceutically acceptable salt, solvate, hydrate, stereoisomer, clathrate, and prodrug thereof. Anthranilic acid derivatives that may be used in methods and compositions disclosed herein include, but are not limited to, Mefenamic acid, Meclofenamic acid, Flufenamic acid, and Tolfenamic acid, and any pharmaceutically acceptable salt, solvate, hydrate, stereoisomer, clathrate, and prodrug thereof. Sulonanilides that may be used in methods and compositions disclosed herein include, but are not limited to, Nimesulide and any pharmaceutically acceptable salt, solvate, hydrate, stereoisomer, clathrate, and prodrug thereof.

Overlapping with the structural classification of NSAIDs is classification of NSAIDs by COX selectivity; NSAIDs may also be classified into selective COX-2 inhibitors or non-selective COX inhibitors. Examples of selective COX-2 inhibitors that may be used in methods and compositions disclosed herein include, but are not limited to, Celecoxib, Rofecoxib, Valdecoxib, Parecoxib, Lumiracoxib, Etoricoxib, and Firocoxib, and any pharmaceutically acceptable salt, solvate, hydrate, stereoisomer, clathrate, and prodrug thereof.

Also contemplated within these classes of NSAIDs are pharmaceutically acceptable salts, solvates, hydrates, stereoisomers (e.g. enantiomers), clathrates, and prodrugs of Salicylates, Propionic acid derivatives, Acetic acid derivatives, Enolic acid (Oxicam) derivatives, Anthranilic acid (Fenamate) derivatives, Selective COX-2 inhibitors, Non-selective COX inhibitors, and Sulfonanilides, and any combination thereof. In some embodiments, the pharmaceutically acceptable salts, solvates, hydrates, stereoisomers (e.g.

enantiomers), clathrates, and prodrugs of Salicylates, Propionic acid derivatives, Acetic acid derivatives, Enolic acid (Oxicam) derivatives, Anthranilic acid (Fenamate) derivatives, Selective COX-2 inhibitors, Nonselective COX inhibitors, and Sulfonanilides are administered as racemic mixtures. In some embodiments the pharmaceutically acceptable salts, solvates, hydrates, stereoisomers (e.g. enantiomers), clathrates, and prodrugs of Salicylates, Propionic acid derivatives, Acetic acid derivatives, Enolic acid (Oxicam) derivatives, Anthranilic acid (Fenamate) derivatives, Selective COX-2 inhibitors, Nonselective COX inhibitors, and Sulfonanilides are administered as single enantiomers (e.g. (R)-ketorolac, (S)-ketorolac).

In some embodiments, the methods provided herein involve the administration or use of an anti-inflammatory agent (e.g. ketorolac derivative) according to formula III or a pharmaceutically acceptable salt, solvate, hydrate, stereoisomer, or clathrate thereof

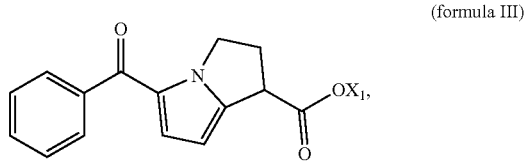

(formula III)

wherein:
X1 is selected from the group consisting of a H, a straight-chain or branched saturated or unsaturated C1-C20 aliphatic group optionally substituted with a C6-C10 aryl group, —NHC6H5, —NHC6H5OCH3, —NHCH2C6H5, —NHCH26H4OCH3, —NHCH2COOCH3, —NHCH2CH2COOC2H5, —NHCH2(CH2)2CH3, —NHC6H10, —NHCH2CH2CH3, —NHCH(CH3)2, —NH(CH2)3OCH3, —NHCH2CH=CH2, optionally substituted talosyl, optionally substituted galactosyl, optionally substituted idosyl, optionally substituted glucosyl, optionally substituted mannosyl, optionally substituted glucosyl, optionally substituted altrosyl, optionally substituted allosyl, optionally substituted alkylpiperidinyl, optionally substituted piperizinyl, optionally substituted alkylpiperazinyl, optionally substituted morpholinyl, and optionally substituted alkylmorpholinyl.

In some embodiments, the anti-inflammatory agent (e.g. ketorolac derivative) according to formula III or a pharmaceutically acceptable salt, solvate, hydrate, stereoisomer, or clathrate thereof is according to formula IV:

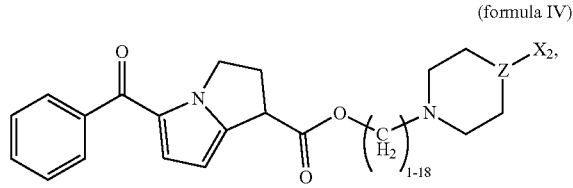

(formula IV)

wherein:
Z is C, N, or O, provided that when Z is O, X2 is absent
X2 is selected from the group consisting of H, a straight-chain or branched saturated or unsaturated C1-C20 aliphatic group, a straight-chain or branched saturated or unsaturated C1-C20 acyl group, and a straight-chain C1-C20 aliphatic alcohol.

Examples of synthesis, chemical structures, and properties of other ketorolac derivatives can be found, e.g., in U.S. Pat. No. 8,551,958B2, US20060183786A1, Qandil et al. Drug Dev Ind Pharm. 2008 October; 34(10):1054-63, Qandil. Int J Mol Sci. 2012; 13(12): 17244-17274, Pawar et al. AAPS PharmSciTech. 2015 June; 16(3): 518-527, Kim et al. Int J Pharm. 2005 Apr. 11; 293(1-2):193-202, and Roy et al. J Pharm Sci. 1994 November; 83(11):1548-53.

In some embodiments, the anti-inflammatory agent (e.g. ketorolac derivative) according to formula III or a pharmaceutically acceptable salt, solvate, hydrate, stereoisomer, or clathrate thereof is according to formula V:

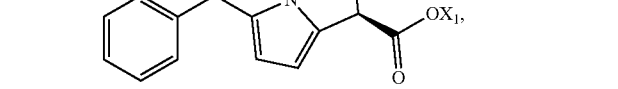

(formula V)

wherein:
X1 is selected from the group consisting of a H, a straight-chain or branched saturated or unsaturated C1-C20 aliphatic group optionally substituted with a C6-C10 aryl group, —NHC6H5, —NHC6H5OCH3, —NHCH2C6H5, —NHCH26H4OCH3, —NHCH2COOCH3, —NHCH2CH2COOC2H5, —NHCH2(CH2)2CH3, —NHC6H10, —NHCH2CH2CH3, —NHCH(CH3)2, —NH(CH2)3OCH3, —NHCH2CH=CH2, optionally substituted talosyl, optionally substituted galactosyl, optionally substituted idosyl, optionally substituted glucosyl, optionally substituted mannosyl, optionally substituted glucosyl, optionally substituted altrosyl, optionally substituted allosyl, optionally substituted alkylpiperidinyl, optionally substituted piperizinyl, optionally substituted alkylpiperazinyl, optionally substituted morpholinyl, and optionally substituted alkylmorpholinyl.

In some embodiments the compound according to formula III or formula IV or a pharmaceutically acceptable salt, solvate, hydrate, stereoisomer, or clathrate thereof is administered alone. In some embodiments, the compound according to formula III or formula IV or a pharmaceutically acceptable salt, solvate, hydrate, stereoisomer, or clathrate thereof is administered in combination with an immunosuppressant (e.g. a nucleoside analog antimetabolite such as cytarabine, or a pharmaceutically acceptable salt, solvate, hydrate, stereoisomer, or clathrate of formulas I or II).

In some embodiments, the anti-inflammatory agent is one of the compounds provided in Table 2, or a pharmaceutically acceptable salt, solvate, hydrate, stereoisomer, or clathrate thereof:

TABLE 2

Exemplary Ketorolac-Related Compounds

| Name | Alternate Name | Chemical Structure |
|---|---|---|
| Ketorolac (free acid) | | 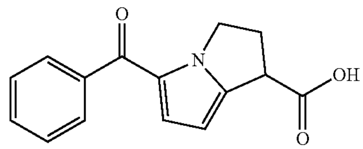 [SMILES: O=C(c1ccccc1)c1ccc2n1CCC2C(=O)O] |
| Ketorolac tromethamine | | 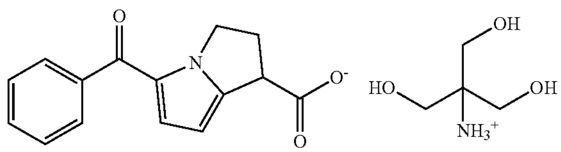 [SMILES: O=C(c1ccccc1)c1ccc2n1CCC2C(=O)[O-] ; [NH3+]C(CO)(CO)CO] |
| Galactosylated ketorolac | | 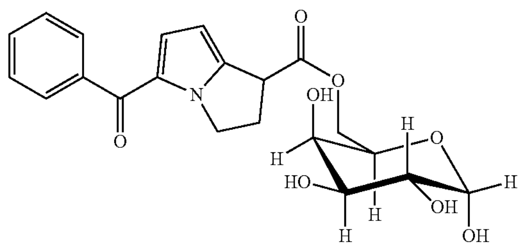 |
| (R)-Ketorolac (free acid) | | 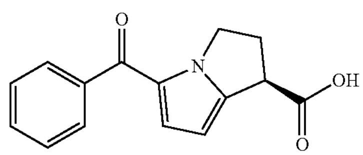 [SMILES: O=C(c1ccccc1)c1ccc2n1CC[C@H]2C(=O)O] |

In some embodiments, the methods or compositions provided herein involve the administration or inclusion of an immunosuppressive agent (e.g. a cytostatic such as a nucleoside analog) in combination with an anti-inflammatory agent (e.g. an NSAID such as an acetic acid derivative). The immunosuppressive agent and the anti-inflammatory agent may be administered simultaneously, separately, or sequentially. In some embodiments, the immunosuppressive agent and the anti-inflammatory agent are administered or present in a composition at a molar ratio of 0.8 (e.g. 0.8:1) to 1,000 (e.g. 1000:1). In some embodiments, the immunosuppressive agent and the anti-inflammatory agent are administered or present in a composition at a molar ratio of at least 0.8. In some embodiments, the immunosuppressive agent and the anti-inflammatory agent are administered or present in a composition at a molar ratio of at most 1,000. In some embodiments, the immunosuppressive agent and the anti-inflammatory agent are administered or present in a composition at a molar ratio of 1,000 to 500, 1,000 to 200, 1,000 to 154.8, 1,000 to 150, 1,000 to 100, 1,000 to 75, 1,000 to 50, 1,000 to 30, 1,000 to 25, 1,000 to 20, 1,000 to 15, 500 to 200, 500 to 154.8, 500 to 150, 500 to 100, 500 to 75, 500 to 50, 500 to 30, 500 to 25, 500 to 20, 500 to 15, 200 to 154.8, 200 to 150, 200 to 100, 200 to 75, 200 to 50, 200 to 30, 200 to 25, 200 to 20,200 to 15, 154.8 to 150, 154.8 to 100, 154.8 to 75, 154.8 to 50, 154.8 to 30, 154.8 to 25, 154.8 to 20, 154.8 to 15, 150 to 100, 150 to 75, 150 to 50, 150 to 30, 150 to 25, 150 to 20, 150 to 15, 100 to 75, 100 to 50, 100 to 30, 100 to 25, 100 to 20, 100 to 15, 75 to 50, 75 to 30, 75 to 25, 75 to 20, 75 to 15, 50 to 30, 50 to 25, 50 to 20, 50 to 15, 30 to 25, 30 to 20, 30 to 15, 25 to 20, 25 to 15, or 20 to 15, 15 to 10, 10 to 9, 10 to 8, 10 to 7, 10 to 6, 10 to 5, 10 to 4, 10 to 3, 10 to 2, 10 to 1.5, 10 to 1, 10 to 0.8, 9 to 8, 9 to 7, 9 to 6, 9 to 5, 9 to 4, 9 to 3, 9 to 2, 9 to 1.5, 9 to 1, 9 to 0.8, 8 to 7, 8 to 6, 8 to 5, 8 to 4, 8 to 3, 8 to 2, 8 to 1.5, 8 to 1, 8 to 0.8, 7 to 6, 7 to 5, 7 to 4, 7 to 3, 7 to 2, 7 to 1.5, 7 to 1, 7 to 0.8, 6 to 5, 6 to 4, 6 to 3, 6 to 2, 6 to 1.5, 6 to 1, 6 to 0.8, 5 to 4, 5 to 3, 5 to 2, 5 to 1.5, 5 to 1, 5 to 0.8, 4 to 3, 4 to 2, 4 to 1.5, 4 to 1, 4 to 0.8, 3 to 2, 3 to 1.5, 3 to 1, 3 to 0.8, 2 to 1.5, 2 to 1, 2 to 0.8, 1.5 to 1, 1.5 to 0.8, or 1 to 0.8. In some embodiments, the immunosuppressive agent and the anti-inflammatory agent are administered or present in a composition at a molar ratio of 1,000, 500, 200, 154.8, 150, 100, 75, 50, 30, 25, 20, 15, 10, 9, 8, 7, 6, 5, 4, 3, 2, 1.5, 1, or 0.8.

In some embodiments, the immunosuppressive agent and the anti-inflammatory agent are administered or present in a composition at a molar ratio of 0.8 (e.g. 0.8:1) to 10 (e.g. 10:1). In some embodiments, the immunosuppressive agent and the anti-inflammatory agent are administered or present in a composition at a molar ratio of at least 0.8. In some embodiments, the immunosuppressive agent and the anti-inflammatory agent are administered or present in a composition at a molar ratio of at most 10. In some embodiments, the immunosuppressive agent and the anti-inflammatory agent are administered or present in a composition at a molar ratio of 10 to 9, 10 to 8, 10 to 7, 10 to 6, 10 to 5, 10 to 4, 10 to 3, 10 to 2, 10 to 1.5, 10 to 1, 10 to 0.8, 9 to 8, 9 to 7, 9 to 6, 9 to 5, 9 to 4, 9 to 3, 9 to 2, 9 to 1.5, 9 to 1, 9 to 0.8, 8 to 7, 8 to 6, 8 to 5, 8 to 4, 8 to 3, 8 to 2, 8 to 1.5, 8 to 1, 8 to 0.8, 7 to 6, 7 to 5, 7 to 4, 7 to 3, 7 to 2, 7 to 1.5, 7 to 1, 7 to 0.8, 6 to 5, 6 to 4, 6 to 3, 6 to 2, 6 to 1.5, 6 to 1, 6 to 0.8, 5 to 4, 5 to 3, 5 to 2, 5 to 1.5, 5 to 1, 5 to 0.8, 4 to 3, 4 to 2, 4 to 1.5, 4 to 1, 4 to 0.8, 3 to 2, 3 to 1.5, 3 to 1, 3 to 0.8, 2 to 1.5, 2 to 1, 2 to 0.8, 1.5 to 1, 1.5 to 0.8, or 1 to 0.8. In some embodiments, the immunosuppressive agent and the anti-inflammatory agent are administered or present in a composition at a molar ratio of 10, 9, 8, 7, 6, 5, 4, 3, 2, 1.5, 1, or 0.8.

In some embodiments, the immunosuppressive agent and the anti-inflammatory agent are administered or present in a composition at a molar ratio of about 0.8 to about 10. In some embodiments, the immunosuppressive agent and the anti-inflammatory agent are administered or present in a composition at a molar ratio of at least about 0.8. In some embodiments, the immunosuppressive agent and the anti-inflammatory agent are administered or present in a composition at a molar ratio of at most about 10. In some embodiments, the immunosuppressive agent and the anti-inflammatory agent are administered or present in a composition at a molar ratio of about 10 to about 9, about 10 to about 8, about 10 to about 7, about 10 to about 6, about 10 to about 5, about 10 to about 4, about 10 to about 3, about 10 to about 2, about 10 to about 1.5, about 10 to about 1, about 10 to about 0.8, about 9 to about 8, about 9 to about 7, about 9 to about 6, about 9 to about 5, about 9 to about 4, about 9 to about 3, about 9 to about 2, about 9 to about 1.5, about 9 to about 1, about 9 to about 0.8, about 8 to about 7, about 8 to about 6, about 8 to about 5, about 8 to about 4, about 8 to about 3, about 8 to about 2, about 8 to about 1.5, about 8 to about 1, about 8 to about 0.8, about 7 to about 6, about 7 to about 5, about 7 to about 4, about 7 to about 3, about 7 to about 2, about 7 to about 1.5, about 7 to about 1, about 7 to about 0.8, about 6 to about 5, about 6 to about 4, about 6 to about 3, about 6 to about 2, about 6 to about 1.5, about 6 to about 1, about 6 to about 0.8, about 5 to about 4, about 5 to about 3, about 5 to about 2, about 5 to about 1.5, about 5 to about 1, about 5 to about 0.8, about 4 to about 3, about 4 to about 2, about 4 to about 1.5, about 4 to about 1, about 4 to about 0.8, about 3 to about 2, about 3 to about 1.5, about 3 to about 1, about 3 to about 0.8, about 2 to about 1.5, about 2 to about 1, about 2 to about 0.8, about 1.5 to about 1, about 1.5 to about 0.8, or about 1 to about 0.8. In some embodiments, the immunosuppressive agent and the anti-inflammatory agent are administered or present in a composition at a molar ratio of about 10, about 9, about 8, about 7, about 6, about 5, about 4, about 3, about 2, about 1.5, about 1, or about 0.8.

If administered separately, the immunosuppressive agent (e.g. a cytostatic such as a nucleoside analog) and the anti-inflammatory agent (e.g. an NSAID such as an acetic acid derivative) are preferentially administered within 24 hours of each other. In some embodiments the immunosuppressive agent and the anti-inflammatory agent are administered within 18, 12, 6, or 2 hours of each other.

V. Therapeutic Agent Formulations/Routes of Administration

The compositions according to the invention (e.g. an anti-inflammatory agent, an immunosuppressant agent, or a combination of an anti-inflammatory and an immunosuppressant agent) may be administered via a variety of routes. In some embodiments, the pharmaceutical composition is formulated for oral administration. In other embodiments, the pharmaceutical composition is formulated for injection. In some embodiments, the pharmaceutical composition is formulated for topical administration.

In some embodiments, the compounds described herein (e.g. an anti-inflammatory agent, an immunosuppressant agent, or a combination of an anti-inflammatory and an immunosuppressant agent, also described herein as "active agents") are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

Orally Administered Forms

In some embodiments, the compositions as described herein are formulated in oral dosage forms. One or more compounds according to the invention (e.g. an anti-inflammatory agent, an immunosuppressant agent, or a combination of an anti-inflammatory and an immunosuppressant agent, also described herein as "active agents") are formulated by combining them with, e.g., pharmaceutically acceptable carriers or excipients. In various embodiments the compounds according to the invention are formulated in oral dosage forms including, by way of example only, tablets, powders, granules, pills, dragees, capsules, liquids, serums, gels, syrups, elixirs, slurries, suspensions, emulsions and the like.

In certain embodiments, pharmaceutical preparations containing the active agents for oral use are obtained by mixing one or more solid excipient with one or more of the compounds described herein, optionally grinding the resulting mixture, and processing the mixture of granules, after adding suitable auxiliaries, if desired, to obtain tablets, pills, or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross linked croscarmellose sodium, polyvinylpyrrolidone, agar, or alginic acid or a salt thereof such as sodium alginate.

In one embodiment, dosage forms, such as dragee cores, pills, and tablets, are provided with one or more suitable coatings. In specific embodiments, concentrated sugar solutions are used for coating the dosage form. The sugar solutions optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of the active agents described herein are formulated into other solid oral dosage forms. Oral dosage forms include push fit capsules made of gelatin, as well as soft, sealed capsules made of gelatin and a plasticizer, such as glycerol or sorbitol. In specific embodiments, push fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, active agents described herein are formulated into oral liquid dosage forms. Exemplary liquid preparations for oral use include solutions, emulsions, serums, syrups or suspensions containing one or more active ingredients in a suitable vehicle. Syrups are clear viscous oral liquids containing high concentrations of sugar or other sweetening agents, in which active agents are solubilized in a pharmaceutically acceptable vehicle. Suspensions consist of finely divided particles of active agent suspended in pharmaceutically acceptable vehicle in which the particles are poorly soluble. Oral emulsions contain liquid forms of active agents dispersed as droplets in a continuous phase of another immiscible vehicle with the help of emulsifying agents (e.g. carbohydrates, gelatin, high molecular weight alcohols, wetting agents, colloidal clays, and the like).

In some embodiments, active agents are formulated into semi-solid oral dosage forms such as gels. Gels or jelly-like formulations have particular relevance for elderly or dysphagic patients with difficulty consuming other oral dosage forms. Gels are formed by adding active agents to water, adding a low critical concentration (e.g. 0.5-2.5%) of a gelling agent, heating, and cooling. Examples of suitable gelling agents include agar, gelatin, carrageenan, sodium caseinate, glycerogelatin, silk fibroin, gellan gum, kelcogel, xyloglucan, gellan, and pectin.

Injectable/Topical Forms

In still other embodiments, the active agents described herein (e.g. an anti-inflammatory agent, an immunosuppressant agent, or a combination of an anti-inflammatory and an immunosuppressant agent) are formulated for parental injection, including formulations suitable for bolus injection or continuous infusion. In specific embodiments, formulations for injection are presented in unit dosage form (e.g., in ampoules) or in multi dose containers. In specific embodiments, the formulations are formulated for intravenous, intramuscular, subcutaneous, or intraperitoneal. Preservatives are, optionally, added to the injection formulations. In still other embodiments, the pharmaceutical compositions are formulated in a form suitable for parenteral injection as sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water soluble form. In additional embodiments, suspensions of the active agents are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

A pharmaceutical composition comprising any one of the pharmaceutical agents described herein may be formulated for sustained or slow release, also called timed release or controlled release. Such compositions may generally be prepared using well known technology and administered by, for example, oral, rectal, intradermal, or subcutaneous implantation, or by implantation at the desired target site. Sustained-release formulations may contain the compound dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of pharmaceutical agent contained within a sustained release formulation depends upon the site of implantation, the rate and expected duration of release, and the nature of the condition, disease or disorder to be treated or prevented.

In still other embodiments, the active agents are administered topically. The compounds described herein are formulated into a variety of topically administrable compositions, such as solutions, suspensions, lotions, gels, foams, serums, pastes, medicated sticks, balms, creams or ointments. Such pharmaceutical compositions optionally contain solubilizers, stabilizers, tonicity enhancing agents, buffers and preservatives.

VI. Methods of Treatment

The compounds and compositions (e.g. an anti-inflammatory agent, immunosuppressant agent, or combination of an anti-inflammatory and an immunosuppressant agent, or compositions thereof) described herein can be used in the preparation of medicaments for the prevention or treatment of cachexia or cachexia-associated diseases or conditions. In addition, a method for treating any of the diseases or conditions described herein in a subject in need of such treatment, involves administration of pharmaceutical compositions containing at least one compound described herein (e.g. an anti-inflammatory agent, an immunosuppressant agent, or a combination of an anti-inflammatory and an immunosuppressant agent), or a pharmaceutically acceptable salt, pharmaceutically acceptable prodrug, pharmaceutically acceptable stereoisomer, or pharmaceutically acceptable solvate thereof, in therapeutically effective amounts to said subject.

Schedule

In some embodiments one or more of the active agents (e.g. anti-inflammatory agents as described herein, immunosuppressant agents as described herein) are administered separately. In some embodiments, the active agents administered separately are administered in separate dosage units (e.g. pills, dragees, tablets). In some embodiments, the active agents administered separately are administered via separate routes of administration. In certain embodiments, one active agent (an immunosuppressive agent or an anti-inflammatory agent) is administered. In certain embodiments, two of the active agents are administered separately.

In certain embodiments, the active agents administered separately are not administered simultaneously.

In certain embodiments, the active agents not administered simultaneously are administered within a defined window. In specific embodiments, the defined window is 48, 36, 24, 12, or 6 hours. In some embodiments one or more, two or more, or three of the active agents are administered within the defined window.

In some embodiments, the active agents or compositions thereof used for treatment are administered for a particular treatment period. In some embodiments, the active agents or compositions thereof are administered for a chronic treatment period, (e.g. for an extended period of time, including throughout the duration of the patient's life) in order to ameliorate or otherwise control or limit the symptoms of the patient's disease or condition. Within the treatment period, the active agents or compositions thereof used for treatment are administered on a particular time schedule. In further embodiments, the active agents or compositions thereof are administered one, two, three, or four times daily. In some embodiments, the active agents or compositions thereof are administered in the morning and evening. In some embodiments, the active agents or compositions thereof are administered one, two, three, or four times weekly. In some embodiments, the active agents or compositions thereof are administered one, two, three, or four times monthly. In some embodiments the active agents or compositions thereof are administered daily for a specific period of time, such as three, four, five, six or seven consecutive days.

In certain embodiments, the methods comprise administering the pharmaceutical agent(s) in at least two treatment cycles. In a specific embodiment, the non-treatment interval may be at least about 2 weeks or between at least about 0.5-12 months, such as at least about one month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months (i.e., 1 year). In certain embodiments, the non-treatment interval is between 1-2 years or between 1-3 years, or longer. In certain embodiments, each treatment course is no longer than about 1 month, no longer than about 2 months, or no longer than about 3 months; or is no longer than 1, 2, 3, 4, 5, 6, 7, 8, 9, 10, 11, 12, 13, 14, 15, 16, 17, 18, 19, 20, 21, 22, 23, 24, 25, 26, 26, 27, 28, 29, 30, or 31 days.

In the case wherein the patient's status does improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from about 10% to about 100%, including, by way of example only, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained (e.g. cancer, immune disorder, cachexia). Patients can, however, require intermittent treatment on a long-term basis upon any recurrence of symptoms.

Dose

In certain embodiments, conditions described for treatment herein (e.g. cancers, immune disorders, cachexia) are treating using anti-inflammatory agents or immunosuppressive agents and doses previously described for administration of the compounds in clinical trials or listed in product packaging as sufficient to achieve anti-inflammatory or immunosuppressive effects. Additionally, doses of anti-inflammatory agents or immunosuppressant agents may be determined by monitoring subject levels of biomarkers of inflammation (e.g. C-reactive protein, IL-6, neutrophil-to-white-blood-cell ratio, neutrophil lymphocyte ratio) and/or biomarkers of immunosuppression (e.g. soluble CD30, T-cell proliferation by PCNA, regulatory T-cell ratio, IL-2, TNFalpha).

In some embodiments, dose for treatment applications is determined in a model organism (e.g. mouse, monkey, canine), and then used to calculate an appropriate dose for treatment in humans. A variety of methods are available to calculate human doses from dosing data determined in other organisms; examples include the dose by factor method (which applies an exponent for body surface area to account for difference in metabolic rate and convert doses between animals and humans) and the allometric scaling method (where the exchange of drug dose is based on normalization of the dose to body surface area), both of which are described e.g. in Nair et al. J Basic Clin Pharm. March 2016-May 2016; 7(2): 27-31.

In some embodiments, applying the dose by factor method involves applying the following equation (Equation 1) to calculate the HED (Human Equivalent Dose) using the no observed adverse effect levels (NOAEL) for drug determined using animal experiments.

$$\text{HED (mg/kg)} = (\text{Animal NOAEL mg/kg}) \times (\text{Weight}_{animal}\ [kg]/\text{Weight}_{human}\ [kg])^{(1-0.67)} \quad \text{(Equation 1)}$$

In some embodiments, applying the allometric scaling method involves applying the following equation (Equation 2) to calculate the HED (Human Equivalent Dose) using the animal dose and correction factor (Km) estimated by dividing the average body weight (kg) of species to its body surface area (m2).

$$\text{HED (mg/kg)} = \text{Animal does (mg/kg)} \times (\text{Animal } Km/\text{Human } Km) \quad \text{(Equation 2)}$$

Immune Disorder Treatment

In one aspect, the disclosure herein provides a method for treating a condition characterized by an immune disorder, comprising administering to a subject in need thereof an effective amount of (i) an immunosuppressive agent, (ii) an anti-inflammatory agent, or both. Immune disorders involve dysfunction in activity of a particular immune process (e.g. over- or under-activity) or representation of one or more components (e.g. particular types of cells) of the immune system. In some embodiments, the immune disorder comprises at least one of the following: (1) increased white blood cell amount, (2) increased neutrophil-to-white-blood-cell ratio, and (3) decreased T-cell-to-white-blood-cell ratio, or (4) any combination thereof. In other embodiments, the immune disorder comprises disorders in specific subtypes of (2), (3), or (4) including but not limited to cytotoxic T-cells, T-helper cells, low-density neutrophils, high density neutrophils, and any combination thereof. In some embodiments, the immune disorder comprises cachexia. In some embodiments, the immune disorder comprises cachexia manifesting with the symptoms of the immune disorder. The immunosuppressive agent and anti-inflammatory agent can comprise any of the immunosuppressive and anti-inflammatory agents described herein (e.g. NSAIDs, cytostatics, antimetabolites, purine antimetabolites, etc).

In certain embodiments, the agent is administered within a treatment cycle, which treatment cycle comprises a treatment course followed by a non-treatment interval. A treatment course of administration refers herein to a finite time frame over which one or more doses of the pharmaceutical agent on one or more days are administered. The finite time frame may be also called herein a treatment window.

In certain embodiments, a method is provided herein for treating an immune disorder (e.g. cachexia) and which method comprises administering to a subject in need thereof an agent or agents (e.g. an anti-inflammatory agent, an immunosuppressant agent, or a combination of an anti-inflammatory and an immunosuppressant agent) in a manner sufficient to (a) decrease white blood cell amount in the subject, (b) decrease neutrophil-to-white-blood-cell ratio in the subject, (c) increase T-cell-to-white-blood-cell ratio in the subject, (d) reverse weight loss/increase weight in the subject; (e) prolong survival time in the subject, or (f) any combination thereof. In some embodiments, the route of administration, dose, or drug form of the agent or agents may be adjusted to modify any of phenotypes (a)-(d), and any combination thereof.

In some embodiments, the method comprises treating the immune disorder (e.g. cachexia) by administering an agents or agents (e.g. an anti-inflammatory agent, an immunosuppressant agent, or a combination of an anti-inflammatory and an immunosuppressant agent) in a manner sufficient to decrease white blood cell amount in the subject by about 10% to about 95%. In some embodiments, the method comprises treating the immune disorder (e.g. cachexia) by administering an agents or agents (e.g. anti-inflammatory agent, immunosuppressive agent, or combination of an anti-inflammatory and immunosuppressant agent) in a manner sufficient to decrease white blood cell amount in the subject by at least about 10%. In some embodiments, the method comprises treating the immune disorder (e.g. cachexia) by administering an agents or agents (e.g. an anti-inflammatory agent, an immunosuppressant agent, or a combination of an anti-inflammatory and an immunosuppressant agent) in a manner sufficient to decrease white blood cell amount in the subject by at most about 95%. In some embodiments, the method comprises treating the immune disorder (e.g. cachexia) by administering an agents or agents (e.g. an anti-inflammatory agent, an immunosuppressant agent, or a combination of an anti-inflammatory and an immunosuppressant agent) in a manner sufficient to decrease white blood cell amount in the subject by about 10% to about 20%, about 10% to about 30%, about 10% to about 40%, about 10% to about 50%, about 10% to about 60%, about 10% to about 70%, about 10% to about 80%, about 10% to about 90%, about 10% to about 95%, about 20% to about 30%, about 20% to about 40%, about 20% to about 50%, about 20% to about 60%, about 20% to about 70%, about 20% to about 80%, about 20% to about 90%, about 20% to about 95%, about 30% to about 40%, about 30% to about 50%, about 30% to about 60%, about 30% to about 70%, about 30% to about 80%, about 30% to about 90%, about 30% to about 95%, about 40% to about 50%, about 40% to about 60%, about 40% to about 70%, about 40% to about 80%, about 40% to about 90%, about 40% to about 95%, about 50% to about 60%, about 50% to about 70%, about 50% to about 80%, about 50% to about 90%, about 50% to about 95%, about 60% to about 70%, about 60% to about 80%, about 60% to about 90%, about 60% to about 95%, about 70% to about 80%, about 70% to about 90%, about 70% to about 95%, about 80% to about 90%, about 80% to about 95%, or about 90% to about 95%. In some embodiments, the method comprises treating the immune disorder (e.g. cachexia) by administering an agents or agents (e.g. an anti-inflammatory agent, an immunosuppressant agent, or a combination of an anti-inflammatory and an immunosuppressant agent) in a manner sufficient to decrease white blood cell amount in the subject by about 10%, about 20%, about 30%, about 40%, about 50%, about 60%, about 70%, about 80%, about 90%, or about 95%.

In some embodiments, the method comprises treating the immune disorder (e.g. cachexia) by administering an agents or agents (e.g. an anti-inflammatory agent, an immunosuppressant agent, or a combination of an anti-inflammatory and an immunosuppressant agent) in a manner sufficient to decrease neutrophil-to-white-blood-cell ratio in the subject by about 10% to about 95%. In some embodiments, the method comprises treating the immune disorder (e.g. cachexia) by administering an agents or agents (e.g. an anti-inflammatory agent, an immunosuppressant agent, or a combination of an anti-inflammatory and an immunosuppressant agent) in a manner sufficient to decrease neutrophil-to-white-blood-cell ratio in the subject by at least about 10%. In some embodiments, the method comprises treating the immune disorder (e.g. cachexia) by administering an agents or agents (e.g. an anti-inflammatory agent, an immunosuppressant agent, or a combination of an anti-inflammatory and an immunosuppressant agent) in a manner sufficient to decrease neutrophil-to-white-blood-cell ratio in the subject by at most about 95%. In some embodiments, the method comprises treating the immune disorder (e.g. cachexia) by administering an agents or agents (e.g. an anti-inflammatory agent, an immunosuppressant agent, or a combination of an anti-inflammatory and an immunosuppressant agent) in a manner sufficient to decrease neutrophil-to-white-blood-cell ratio in the subject by about 10% to about 20%, about 10% to about 30%, about 10% to about 40%, about 10% to about 50%, about 10% to about 60%, about 10% to about 70%, about 10% to about 80%, about 10% to about 90%, about 10% to about 95%, about 20% to about 30%, about 20% to about 40%, about 20% to about 50%, about 20% to about 60%, about 20% to about 70%, about 20% to about 80%, about 20% to about 90%, about 20% to about 95%, about 30% to about 40%, about 30% to about 50%, about 30% to about 60%, about 30% to about 70%, about 30% to about 80%, about 30% to about 90%, about 30% to about 95%, about 40% to about 50%, about 40% to about 60%, about 40% to about 70%, about 40% to about 80%, about 40% to about 90%, about 40% to about 95%, about 50% to about 60%, about 50% to about 70%, about 50% to about 80%, about 50% to about 90%, about 50% to about 95%, about 60% to about 70%, about 60% to about 80%, about 60% to about 90%, about 60% to about 95%, about 70% to about 80%, about 70% to about 90%, about 70% to about 95%, about 80% to about 90%, about 80% to about 95%, or about 90% to about 95%. In some embodiments, the method comprises treating the immune disorder (e.g. cachexia) by administering an agents or agents (e.g. an anti-inflammatory agent, an immunosuppressant agent, or a combination of an anti-inflammatory and an immunosuppressant agent) in a manner sufficient to decrease neutrophil-to-white-blood-cell ratio in the subject by about 10%, about 20%, about 30%, about 40%, about 50%, about 60%, about 70%, about 80%, about 90%, or about 95%.

In some embodiments, administering an agents or agents (e.g. an anti-inflammatory agent, an immunosuppressant agent, or a combination of an anti-inflammatory and an immunosuppressant agent) is effective to increase body weight of the subject by about 110% to about 170%. In some embodiments, administering an agents or agents (e.g. an anti-inflammatory agent, an immunosuppressant agent, or a combination of an anti-inflammatory and an immunosuppressant agent) is effective to increase body weight of the subject by at least about 110%. In some embodiments, administering an agents or agents (e.g. an anti-inflammatory agent, an immunosuppressant agent, or a combination of an anti-inflammatory and an immunosuppressant agent) is effective to increase body weight of the subject by at most about 170%. In some embodiments, administering an agents or agents (e.g. an anti-inflammatory agent, an immunosuppressant agent, or a combination of an anti-inflammatory and an immunosuppressant agent) is effective to increase body weight of the subject by about 110% to about 120%, about 110% to about 130%, about 110% to about 140%, about 110% to about 150%, about 110% to about 160%, about 110% to about 170%, about 120% to about 130%, about 120% to about 140%, about 120% to about 150%, about 120% to about 160%, about 120% to about 170%, about 130% to about 140%, about 130% to about 150%, about 130% to about 160%, about 130% to about 170%, about 140% to about 150%, about 140% to about 160%, about 140% to about 170%, about 150% to about 160%, about 150% to about 170%, or about 160% to about 170%. In some embodiments, administering an agents or agents (e.g. an anti-inflammatory agent, an immunosuppressant agent, or a combination of an anti-inflammatory and an immunosuppressant agent) is effective to increase body weight of the subject by about 110%, about 120%, about 130%, about 140%, about 150%, about 160%, or about 170%.

In some embodiments, administering an agents or agents (e.g. an anti-inflammatory agent, an immunosuppressant agent, or a combination of an anti-inflammatory and an immunosuppressant agent) is effective to increase body weight of the subject by about 5% to about 170%. In some embodiments, administering an agents or agents (e.g. an anti-inflammatory agent, an immunosuppressant agent, or a combination of an anti-inflammatory and an immunosuppressant agent) is effective to increase body weight of the subject by at least about 5%. In some embodiments, administering an agents or agents (e.g. an anti-inflammatory agent, an immunosuppressant agent, or a combination of an anti-inflammatory and an immunosuppressant agent) is effective to increase body weight of the subject by at most about 170%. In some embodiments, administering an agents or agents (e.g. an anti-inflammatory agent, an immunosuppressant agent, or a combination of an anti-inflammatory and an immunosuppressant agent) is effective to increase body weight of the subject by about 5% to about 25%, about 5% to about 50%, about 5% to about 75%, about 5% to about 100%, about 5% to about 125%, about 5% to about 150%, about 5% to about 170%, about 25% to about 50%, about 25% to about 75%, about 25% to about 100%, about 25% to about 125%, about 25% to about 150%, about 25% to about 170%, about 50% to about 75%, about 50% to about 100%, about 50% to about 125%, about 50% to about 150%, about 50% to about 170%, about 75% to about 100%, about 75% to about 125%, about 75% to about 150%, about 75% to about 170%, about 100% to about 125%, about 100% to about 150%, about 100% to about 170%, about 125% to about 150%, about 125% to about 170%, or about 150% to about 170%. In some embodiments, administering an agents or agents (e.g. an anti-inflammatory agent, an immunosuppressant agent, or a combination of an anti-inflammatory and an immunosuppressant agent) is effective to increase body weight of the subject by about 5%, about 25%, about 50%, about 75%, about 100%, about 125%, about 150%, or about 170%.

In certain embodiments, the method for treating the immune disorder (e.g. cachexia) comprising administering to a subject in need thereof a combination of an anti-inflammatory and an immunosuppressant agent (e.g. ketorolac and cytarabine) counteracts the side effects of monoadministration of an immunosuppressant agent alone (e.g. cytarabine). In some embodiments, the side effect is transient weight loss. In some embodiments, the transient weight loss counteracted is about 1%, 2%, 3%, 4%, 5%, 6%, 7%, 8%, 9%, 10%, 11%, 12%, 13%, 14%, 15%, 16%, 17%, 18%, 19%, or 20% of pre-treatment body weight. In some embodiments, the transient weight loss counteracted persists for no more than 1, no more than 2, no more than 3, no more than 4, or no more than 5 days post-treatment.

In some embodiments, the method comprises treating the immune disorder (e.g. cachexia) by administering an agents or agents (e.g. an anti-inflammatory agent, an immunosuppressant agent, or a combination of an anti-inflammatory and an immunosuppressant agent) in a manner sufficient to prolong survival time of the subject by about 10% to about 1,000%. In some embodiments, the method comprises treating the immune disorder (e.g. cachexia) by administering an agents or agents (e.g. an anti-inflammatory agent, an immunosuppressant agent, or a combination of an anti-inflammatory and an immunosuppressant agent) in a manner sufficient to prolong survival time of the subject by at least about 10%. In some embodiments, the method comprises treating the immune disorder (e.g. cachexia) by administering an agents or agents (e.g. an anti-inflammatory agent, an immunosuppressant agent, or a combination of an anti-inflammatory and an immunosuppressant agent) in a manner sufficient to prolong survival time of the subject by at most about 100%. In some embodiments, the method comprises treating the immune disorder (e.g. cachexia) by administering an agents or agents (e.g. an anti-inflammatory agent, an immunosuppressant agent, or a combination of an anti-inflammatory and an immunosuppressant agent) in a manner sufficient to prolong survival time of the subject by at most about 1,000%. In some embodiments, the method comprises treating the immune disorder (e.g. cachexia) by administering an agents or agents (e.g. an anti-inflammatory agent, an immunosuppressant agent, or a combination of an anti-inflammatory and an immunosuppressant agent) in a manner sufficient to prolong survival time of the subject by about 10% to about 20%, about 10% to about 30%, about 10% to about 40%, about 10% to about 50%, about 10% to about 60%, about 10% to about 70%, about 10% to about 80%, about 10% to about 90%, about 10% to about 100%, about 20% to about 30%, about 20% to about 40%, about 20% to about 50%, about 20% to about 60%, about 20% to about 70%, about 20% to about 80%, about 20% to about 90%, about 20% to about 100%, about 30% to about 40%, about 30% to about 50%, about 30% to about 60%, about 30% to about 70%, about 30% to about 80%, about 30% to about 90%, about 30% to about 100%, about 40% to about 50%, about 40% to about 60%, about 40% to about 70%, about 40% to about 80%, about 40% to about 90%, about 40% to about 100%, about 50% to about 60%, about 50% to about 70%, about 50% to about 80%, about 50% to about 90%, about 50% to about 100%, about 60% to about 70%, about 60% to about 80%, about 60% to about 90%, about 60% to about 100%, about 70% to about 80%, about 70% to about 90%, about 70% to about 100%, about 80% to about 90%, about 80% to about 100%, about 90% to about 100%, about 100% to about 150%, about 100% to about 200%, about 100% to about 250%, about 100% to about 300%, about 100% to about 500%, about 100% to about 1,000%, about 150% to about 200%, about 150% to about 250%, about 150% to about 300%, about 150% to about 500%, about 150% to about 1,000%, about 200% to about 250%, about 200% to about 300%, about 200% to about 500%, about 200% to about 1,000%, about 250% to about 300%, about 250% to about 500%, about 250% to about 1,000%, about 300% to about 500%, about 300% to about 1,000%, or about 500% to about 1,000%. In some embodiments, the method comprises treating the immune disorder (e.g. cachexia) by administering an agents or agents (e.g. an anti-inflammatory agent, an immunosuppressant agent, or a combination of an anti-inflammatory and an immunosuppressant agent) in a manner sufficient to prolong survival time of the subject by about 10%, about 20%, about 30%, about 40%, about 50%, about 60%, about 70%, about 80%, about 90%, or about 100%, about 150%, about 200%, about 250%, about 300%, about 500%, or about 1,000%.

Treatment of Condition Accompanying Cachexia

In one aspect, the disclosure herein provides a method for treating a method for treating a subject suffering from a primary condition accompanying cachexia, comprising alternatively administering to the subject in need thereof: an effective amount of (i) an immunosuppressive agent, (ii) an anti-inflammatory agent, or both; and an effective amount of an agent for treating the primary condition. The immunosuppressive agent and anti-inflammatory agent can comprise any of the immunosuppressive and anti-inflammatory agents described herein (e.g. NSAIDs, cytostatics, antimetabolites, purine antimetabolites, etc).

"Alternatively administering" means that the administration of the agent(s) for treating cachexia and that of the agent(s) for treating the primary condition are in the form of one after another, optionally with a nontreatment period there between, and are optionally repeated for a certain number of cycles. Alternatively administering can comprise various different embodiments. For example, treatment for cachexia as disclosed herein and the treatment for the primary condition can be administered in any order. In some embodiments, the treatment for cachexia as disclosed herein is administered first for a certain period of time followed by the treatment for the primary condition for another period of time. In other embodiments, the agent for treating the primary condition is administered first for a certain period of time followed by the treatment for cachexia for another period of time. In some embodiments, the two treatments are separated by a drug holiday wherein no treatment is administered. The length of the drug holiday can vary between 1 or 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days.

In some embodiments, the primary condition accompanying cachexia is any chronic/serious disease known to result in cachexia, such as a tumor, AIDS, sepsis, severe trauma, chronic obstructive pulmonary disease, multiple sclerosis, congestive heart failure, tuberculosis, familial amyloid polyneuropathy, chronic kidney disease, cystic fibrosis, or Type I diabetes, and any combination thereof. In some cases, the treatment protocol described herein (e.g. combination of an immunosuppressant agent and an anti-inflammatory agent) improves treatment of the primary condition. Administration of the protocol for treating the primary condition accompanying cachexia (e.g. combination of an immunosuppressant agent and an anti-inflammatory agent) may improve survival in response to the treatment for the primary disease. Administration of the protocol for treating the primary condition accompanying cachexia (e.g. combination of an immunosuppressant agent and an anti-inflammatory agent) may decrease the amount of time between cycles of treatment for the primary disease, when treatment for the primary disease comprises a treatment period alternating with a non-treatment period. Administration of the protocol for treating the primary condition accompanying cachexia (e.g. combination of an immunosuppressant agent and an anti-inflammatory agent) may decrease the number of cycles of treatment for the primary disease that can be administered safely to the subject, when treatment for the primary disease involves alternating treatment and non-treatment cycles, and the number of treatment cycles is limited by the toxicity of drugs for treating the primary condition accompanying cachexia.

In certain embodiments, the effective amount of (i) an immunosuppressive agent, (ii) an anti-inflammatory agent, or both is administered for at least two treatment cycles in the method of treating the primary condition accompanying cachexia. In a specific embodiment, the non-treatment interval may be at least about 2 weeks or between at least about 0.5-12 months, such as at least about one month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months (i.e., 1 year). In certain embodiments, the non-treatment interval is between 1-2 years or between 1-3 years, or longer. In certain embodiments, each treatment course is no longer than about 1 month, no longer than about 2 months, or no longer than about 3 months; or is no longer than 1, 2, 3, 4, 5, 6, 7, 8, 9, 10, 11, 12, 13, 14, 15, 16, 17, 18, 19, 20, 21, 22, 23, 24, 25, 26, 26, 27, 28, 29, 30, or 31 days.

In certain cases, the method of treating the primary condition accompanying cachexia may comprise a number of alternating cycles of (a) treatment for cachexia and (b) treatment for the primary condition. In some embodiments, the method of treating the primary condition accompanying cachexia comprises 1 cycle to 10 cycles. In some embodiments, the method of treating the primary condition accompanying cachexia comprises at least 1 cycle. In some embodiments, the method of treating the primary condition accompanying cachexia comprises at most 10 cycles. In some embodiments, the method of treating the primary condition accompanying cachexia comprises 1 cycle to 2 cycles, 1 cycle to 3 cycles, 1 cycle to 4 cycles, 1 cycle to 5 cycles, 1 cycle to 6 cycles, 1 cycle to 7 cycles, 1 cycle to 8 cycles, 1 cycle to 9 cycles, 1 cycle to 10 cycles, 2 cycles to 3 cycles, 2 cycles to 4 cycles, 2 cycles to 5 cycles, 2 cycles to 6 cycles, 2 cycles to 7 cycles, 2 cycles to 8 cycles, 2 cycles to 9 cycles, 2 cycles to 10 cycles, 3 cycles to 4 cycles, 3 cycles to 5 cycles, 3 cycles to 6 cycles, 3 cycles to 7 cycles, 3 cycles to 8 cycles, 3 cycles to 9 cycles, 3 cycles to 10 cycles, 4 cycles to 5 cycles, 4 cycles to 6 cycles, 4 cycles to 7 cycles, 4 cycles to 8 cycles, 4 cycles to 9 cycles, 4 cycles to 10 cycles, 5 cycles to 6 cycles, 5 cycles to 7 cycles, 5 cycles to 8 cycles, 5 cycles to 9 cycles, 5 cycles to 10 cycles, 6 cycles to 7 cycles, 6 cycles to 8 cycles, 6 cycles to 9 cycles, 6 cycles to 10 cycles, 7 cycles to 8 cycles, 7 cycles to 9 cycles, 7 cycles to 10 cycles, 8 cycles to 9 cycles, 8 cycles to 10 cycles, or 9 cycles to 10 cycles. In some embodiments, the method of treating the primary condition accompanying cachexia comprises 1 cycle, 2 cycles, 3 cycles, 4 cycles, 5 cycles, 6 cycles, 7 cycles, 8 cycles, 9 cycles, or 10 cycles.

In certain embodiments the effective amount of an agent for treating the primary condition accompanying cachexia is administered for at least two treatment cycles in the method of treating the primary condition accompanying cachexia. In a specific embodiment, the non-treatment interval may be at least about 2 weeks or between at least about 0.5-12 months, such as at least about one month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months (i.e., 1 year). In certain embodiments, the non-treatment interval is between 1-2 years or between 1-3 years, or longer. In certain embodiments, each treatment course is no longer than about 1 month, no longer than about 2 months, or no longer than about 3 months; or is no longer than 1, 2, 3, 4, 5, 6, 7, 8, 9, 10, 11, 12, 13, 14, 15, 16, 17, 18, 19, 20, 21, 22, 23, 24, 25, 26, 26, 27, 28, 29, 30, or 31 days.

The agent for treating the primary condition accompanying cachexia may be any pharmaceutically acceptable agent approved for treating the primary condition accompanying cachexia. In the case where the primary condition is a tumor or cancer, pharmaceutically acceptable agents include chemotherapy regimens (e.g. combinations of agents), including but not limited to 7+3, ABVD, AC, BACOD, BEACOPP, BEP, CA, CAF, CAPOX, CAV, CBV, CHOEP, CEPP, ChlVPP/EVA, CHOP, R-CHOP, ClaPD, CMF, CMV, COP or CVP, COPP, CT or TC, CTD, CVAD, CVE, CYBORD, DA or DAC, DAT, DCEP, DHAP, DHAP-R, DICE, DT-PACE, EC, ECF, EOX, EP, EPOCH, EPOCH-R, ESHAP, ESHAP-R, FAM, FAMTX, FCM, FCM-R, FCR, FM, FM-R, FEC, FL (also known as Mayo), FLAG, FLAG-Ida, FLAG-Mito, FLAMSA, FLAMSA-BU, FLAMSA-MEL, FOLFIRI, FOLFIRINOX, FOLFOX, GC, GDP, GemOx, GVD, GemOx-R, IAC, ICE, ICE-R, IFL, IVA, m-BACOD, MACOP-B, MAID, MINE, MINE-R, MMM, MOPP, MVAC, MVP, NP, PACE, PCV, PEB, PEI, POMP, ProM-ACE-MOPP, ProMACE-CytaBOM, RdC, R-Benda, R-DHAP, R-FCM, R-ICE, RVD, Stanford V, TAC, TAD, TC or CT, TCH, Thal/Dex, TIP, EE-4A, DD-4A, VABCD, VAC, VAD, VAMP, Regimen I, VAPEC-B, VD-PACE, VIFUP, VIP, and VTD-PACE, and any combination thereof. In the case where the primary condition is a tumor or cancer, pharmaceutically acceptable agents include one or more alkylating agents (e.g. Cyclophosphamide, Mechlorethamine, Chlorambucil, Melphalan, Dacarbazine), anthracyclines (e.g. Daunorubicin, Doxorubicin, Epirubicin, Idarubicin, Mitoxantrone, Valrubicin), cytoskeletal disruptors (e.g. Paclitaxel, Docetaxel, Abraxane, Taxotere), epothilones (e.g. ixabepilone), histone deacetylase inhibitors (e.g. Vorinostat, Romidepsin), topoisomerase I inhibitors (e.g. Irinotecan, Topotecan), topoisomerase II inhibitors (e.g. Etoposide, Teniposide, Tafluposide), kinase inhibitors (e.g. Bortezomib, Erlotinib, Gefitinib, Imatinib, Vemurafenib, Vismodegib), peptide antibiotics (e.g. Bleomycin, Actinomycin), retinoids (e.g. Tretinoin, Alitretinoin, Bexarotene), or vinca alkaloids or derivatives of vinca alkaloids (e.g. Vinblastine, Vincristine, Vindesine, Vinorelbine). In the case where the primary condition is a tumor or cancer, pharmaceutically acceptable agents include one or more approved chemotherapy agents such as cyclophosphamide, ifosfamide, mesna, methotrexate, mitomycin, etoposide, irinotecan, mitoxantrone, epirubicin, fludarabine, G-CSF, amsacrine, leucovorin, topotecan, hydroxydaunorubicin, vincristine, bleomycin, dacarbazine, procarbazine, thalidomide, fluorouracil, cisplatin, oxaliplatin, carboplatin, tioguanine, capecitabine, gemcitabine, vinorelbine, 6-mercaptopurine, fluorouracil, bendamustine, carmustine, chlorambucil, docetaxel, paclitaxel, bortezomib, and hydroxyurea, and any combination thereof.

In the case where the primary condition is an autoimmune disease (e.g. Crohn's, Rheumatoid Arthritis, systemic lupus erythematosus) pharmaceutically acceptable agents include disease-modifying antirheumatic drugs (DMARDS, e.g. hydroxychloroquine, methotrexate, azathioprine) and anti-TNF agents (e.g. infliximab, adalimumab, certolizumab pegol, golimumab, etanercept).

In the case where the primary condition is AIDS, pharmaceutically acceptable agents include nucleotide reverse transcriptase inhibitors (NRTIs, e.g. Abacavir, Didanosine, Emtricitabine, Lamivudine, Stavudine, Tenofovir, Zalcitabine, Zidovudine), protease inhibitors (PIs, e.g. Amprenavir, Atazanavir, Fosamprenavir, Indinavir, Lopinavir, Ritonavir, Saquinavir), and any combination thereof (e.g. Highly Active Antiretroviral Therapy/HAART).

In some embodiments, the method of treating the primary condition accompanying cachexia can prolong survival time of the subject by about 10% to about 1,000%. In some embodiments, the method of treating the primary condition accompanying cachexia can prolong survival time of the subject by at least about 10%. In some embodiments, the method of treating the primary condition accompanying cachexia can prolong survival time of the subject by at most about 100%. In some embodiments, the method of treating the primary condition accompanying cachexia can prolong survival time of the subject by at most about 1,000%. In some embodiments, the method of treating the primary condition accompanying cachexia can prolong survival time of the subject by about 10% to about 20%, about 10% to about 30%, about 10% to about 40%, about 10% to about 50%, about 10% to about 60%, about 10% to about 70%, about 10% to about 80%, about 10% to about 90%, about 10% to about 100%, about 20% to about 30%, about 20% to about 40%, about 20% to about 50%, about 20% to about 60%, about 20% to about 70%, about 20% to about 80%, about 20% to about 90%, about 20% to about 100%, about 30% to about 40%, about 30% to about 50%, about 30% to about 60%, about 30% to about 70%, about 30% to about 80%, about 30% to about 90%, about 30% to about 100%, about 40% to about 50%, about 40% to about 60%, about 40% to about 70%, about 40% to about 80%, about 40% to about 90%, about 40% to about 100%, about 50% to about 60%, about 50% to about 70%, about 50% to about 80%, about 50% to about 90%, about 50% to about 100%, about 60% to about 70%, about 60% to about 80%, about 60% to about 90%, about 60% to about 100%, about 70% to about 80%, about 70% to about 90%, about 70% to about 100%, about 80% to about 90%, about 80% to about 100%, about 90% to about 100%, about 100% to about 150%, about 100% to about 200%, about 100% to about 250%, about 100% to about 300%, about 100% to about 500%, about 100% to about 1,000%, about 150% to about 200%, about 150% to about 250%, about 150% to about 300%, about 150% to about 500%, about 150% to about 1,000%, about 200% to about 250%, about 200% to about 300%, about 200% to about 500%, about 200% to about 1,000%, about 250% to about 300%, about 250% to about 500%, about 250% to about 1,000%, about 300% to about 500%, about 300% to about 1,000%, or about 500% to about 1,000%. In some embodiments, the method of treating the primary condition accompanying cachexia can prolong survival time of the subject by about 10%, about 20%, about 30%, about 40%, about 50%, about 60%, about 70%, about 80%, about 90%, or about 100%, about 150%, about 200%, about 250%, about 300%, about 500%, or about 1,000%.

Kits

The present invention further comprises kits that are suitable for use in performing the methods of treatment described above (e.g. method of treating an immune disorder or method of treating a primary disorder accompanying cachexia). In one embodiment, the kit contains a dosage form comprising one or more immunosuppressant agents as described above (e.g. purine nucleotide analogs) in quantities sufficient to carry out the methods of the present invention. Preferably, the dosage form comprises an effective amount of the immunosuppressant to treat an immune disorder selected from the group consisting of (1) increased white blood cell amount, (2) increased neutrophil-to-white-blood-cell ratio, and (3) decreased T-cell-to-white-blood-cell ratio, and any combination thereof. In another embodiment, the kit contains a first dosage form comprising one or more immunosuppressant agents as described above and a second dosage form comprising one or more anti-inflammatory agents as described above in quantities sufficient to carry out the methods of the present invention. Preferably, the first dosage form and the second dosage form together comprise a therapeutically effective amount of the immunosuppressant agent and anti-inflammatory agent for treating an immune disorder selected from the group consisting of (1) increased white blood cell amount, (2) increased neutrophil-to-white-blood-cell ratio, and (3) decreased T-cell-to-white-blood-cell ratio, and any combination thereof. In some embodiments, the one or more immunosuppressant agents is cytarabine or a pharmaceutically acceptable salt, solvate, hydrate, stereoisomer, clathrate, or prodrug thereof. In some embodiments, the one or more anti-inflammatory agents is ketorolac or a pharmaceutically acceptable salt, solvate, hydrate, stereoisomer, clathrate, or prodrug thereof. In some embodiments, the dosage forms additionally comprise a pharmaceutically acceptable excipient.

In yet another embodiment, the kit contains (i) a first dosage form comprising one or more immunosuppressant agents as described above and a second dosage form comprising one or more anti-inflammatory agents as described above in quantities sufficient to carry out the methods of the present invention (e.g. treatment for the immune disorder); and (ii) a third dosage form comprising one or more agents for treating a primary condition accompanying cachexia as described above. In preferred embodiments, the first, second, and third dosage forms comprise therapeutically effective amounts of their corresponding agents. In some embodiments, the one or more immunosuppressant agents is cytarabine or a pharmaceutically acceptable salt, solvate, hydrate, stereoisomer, clathrate, or prodrug thereof. In some embodiments, the one or more anti-inflammatory agents is ketorolac or a pharmaceutically acceptable salt, solvate, hydrate, stereoisomer, clathrate, or prodrug thereof. In some embodiments, the one or more agents for treating a primary condition accompanying cachexia is a chemotherapy agent. In some embodiments, the chemotherapy agent is selected from the group consisting of cyclophosphamide, ifosfamide, mesna, methotrexate, mitomycin, etoposide, irinotecan, mitoxantrone, epirubicin, fludarabine, G-CSF, amsacrine, leucovorin, topotecan, hydroxydaunorubicin, vincristine, bleomycin, dacarbazine, procarbazine, thalidomide, fluorouracil, cisplatin, oxaliplatin, carboplatin, tioguanine, capecitabine, gemcitabine, vinorelbine, 6-mercaptopurine, fluorouracil, bendamustine, carmustine, chlorambucil, docetaxel, paclitaxel, bortezomib, and hydroxyurea, and any combination thereof. In some embodiments, the dosage forms additionally comprise a pharmaceutically acceptable excipient.

The following non-limiting embodiments provide illustrative examples of the invention, but do not limit the scope of the invention:

Embodiment 1

A method for treating an immune disorder characterized by (1) increased white blood cell amount, (2) increased neutrophil-to-white-blood-cell ratio, and (3) decreased T-cell-to-white-blood-cell ratio, comprising administering to a subject in need thereof an effective amount of an immunosuppressive agent, provided that the immunosuppressive agent is not cytarabine or a pharmaceutically acceptable salt, solvate, hydrate, stereoisomer, clathrate, or prodrug thereof.

Embodiment 2

A method for treating an immune disorder characterized by (1) increased white blood cell amount, (2) increased neutrophil-to-white-blood-cell ratio, and (3) decreased T-cell-to-white-blood-cell ratio, comprising administering to a subject in need thereof an effective amount of an anti-inflammatory agent, provided that the anti-inflammatory agent is not ketorolac or a pharmaceutically acceptable salt, solvate, hydrate, stereoisomer, clathrate, or prodrug thereof.

Embodiment 3

A method for treating an immune disorder characterized by (1) increased white blood cell amount, (2) increased neutrophil-to-white-blood-cell ratio, and (3) decreased T-cell-to-white-blood-cell ratio, comprising administering to a subject in need thereof an effective amount of (i) an immunosuppressive agent, and (ii) an anti-inflammatory agent, provided that when the immunosuppressive agent is cytarabine or a pharmaceutically acceptable salt, solvate, hydrate, stereoisomer, clathrate, or prodrug thereof the anti-inflammatory agent is not ketorolac or a pharmaceutically acceptable salt, solvate, hydrate, stereoisomer, clathrate, or prodrug thereof.

Embodiment 4

A method for treating cachexia, comprising administering to a subject in need thereof an effective amount of an agent selected from the group consisting of an immunosuppressive agent, provided that the immunosuppressive agent is not cytarabine or a pharmaceutically acceptable salt, solvate, hydrate, stereoisomer, clathrate, or prodrug thereof.

Embodiment 5

A method for treating cachexia, comprising administering to a subject in need thereof an effective amount of an agent selected from the group consisting of an anti-inflammatory agent, provided that the anti-inflammatory agent is not ketorolac or a pharmaceutically acceptable salt, solvate, hydrate, stereoisomer, clathrate, or prodrug thereof.

Embodiment 6

A method for treating cachexia, comprising administering to a subject in need thereof an effective amount of an agent selected from the group consisting of (i) an immunosuppressive agent, and (ii) an anti-inflammatory agent, provided that when the immunosuppressive agent is cytarabine or a pharmaceutically acceptable salt, solvate, hydrate, stereoisomer, clathrate, or prodrug thereof the anti-inflammatory agent is not ketorolac or a pharmaceutically acceptable salt, solvate, hydrate, stereoisomer, clathrate, or prodrug thereof.

Embodiment 7

The method of any of embodiments 1 to 3, wherein the immune disorder is further characterized by wasting symptoms.

Embodiment 8

The method of embodiment 7, wherein the wasting symptoms comprise fluid-corrected weight loss and at least three or more symptoms selected from the group consisting of decreased muscle strength, fatigue, anorexia, low fat-free mass index, and abnormal biochemistry as exhibited by increased inflammatory markers, anemia, or low serum albumin, and any combination thereof.

Embodiment 9

The method of any one of embodiments 1 to 8, wherein the immune disorder is induced by chronic disease.

Embodiment 10

The method of embodiment 9, wherein the chronic disease is selected from the group consisting of AIDS, chronic obstructive pulmonary disease, multiple sclerosis, congestive heart failure, tuberculosis, familial amyloid polyneuropathy, chronic kidney disease, and cystic fibrosis.

Embodiment 11

The method of embodiment 9, wherein the chronic disease is cancer.

Embodiment 12

The method of any one of embodiments 1-11, wherein the immunosuppressive agent is a pyrimidine nucleoside antimetabolite.

Embodiment 13

The method of any one of embodiments 1-12, wherein the anti-inflammatory agent is an NSAID.

Embodiment 14

The method of embodiment 13, wherein the NSAID is a nonselective COX inhibitor.

Embodiment 15

The method of embodiment 14, wherein the nonselective COX inhibitor is an acetic acid derivative.

Embodiment 16

The method of embodiment 15, wherein the acetic acid derivative is indomethacin, diclofenac, tolmetin, aceclofenac, sulindac, nabumetone, etodolac, or a pharmaceutically acceptable salt, solvate, hydrate, stereoisomer, clathrate, or prodrug thereof.

Embodiment 17

The method of any one of embodiments 1-16, wherein the immunosuppressive agent and the anti-inflammatory agent are administered at a molar ratio of about 20:1 to about 0.8:1.

Embodiment 18

The method of any one of embodiments 1-17, wherein the immunosuppressive agent and the anti-inflammatory agent are administered in the same composition.

Embodiment 19

The method of any one of embodiments 1-18, wherein the immunosuppressive agent and the anti-inflammatory agent are administered in separate compositions.

Embodiment 20

The method of any one of embodiments 1-17, wherein the immunosuppressive agent and the anti-inflammatory agent are administered via separate administration routes.

Embodiment 21

The method of any one of embodiments 1-17, wherein the immunosuppressive agent and the anti-inflammatory agent are administered within 24 hours of each other.

Embodiment 22

The method of any one of embodiments 1-21, wherein one or more of the immunosuppressive agent and the anti-inflammatory agent are administered orally.

Embodiment 23

The method of any one of embodiments 1-22, wherein one or more of the immunosuppressive agent and the anti-inflammatory agent are administered parenterally.

Embodiment 24

The method of any one of embodiments 1-23, wherein the method:
(a) effectively decreases the white blood cell amount of the subject by at least about 10%;
(b) effectively decreases the neutrophil-to-white-blood-cell ratio of the subject by at least about 10%; and
(c) effectively increases the T-cell-to-white-blood-cell ratio of the subject by at least about 10%.

Embodiment 25

The method of any one of embodiments 1-24, wherein the method effectively increases the body weight of the subject by at least about 10%.

Embodiment 26

A method for treating a subject suffering from a primary condition accompanying cachexia, comprising alternatively administering to the subject in need thereof: (i) an effective amount of an immunosuppressive agent, and an anti-inflammatory agent, provided that when the immunosuppressive agent is cytarabine or a pharmaceutically acceptable salt, solvate, hydrate, stereoisomer, clathrate, or prodrug thereof the anti-inflammatory agent is not ketorolac or a pharmaceutically acceptable salt, solvate, hydrate, stereoisomer, clathrate, or prodrug thereof; and (ii) an additional agent in an effective amount for treating the primary condition, wherein the primary condition is cancer.

Embodiment 27

The method of embodiment 26, wherein the immunosuppressive agent is cytarabine or cytarabine hydrochloride.

Embodiment 28

The method of embodiment 26, wherein the anti-inflammatory agent is ketorolac tromethamine.

Embodiment 29

The method of any one of embodiments 26 to 28, wherein the immunosuppressive agent and the anti-inflammatory agent are administered within 24 hours of each other.

Embodiment 30

The method of any one of embodiments 26-29, wherein (i) and (ii) are separated by a non-treatment interval of at least 1 week.

Embodiment 31

A method for screening an agent or a combination of agents for treating cachexia, comprising identifying the agent or the combination of agents capable of decreasing white blood cell amount, decreasing neutrophil ratio, and/or increasing T cell ratio.

Embodiment 32

The method of embodiment 31, wherein the agent or the combination of agents is capable of decreasing the white blood cell amount by at least 10%.

Embodiment 33

The method of embodiment 31, wherein the agent or the combination of agents is capable of decreasing the neutrophil ratio by at least 10%.

Embodiment 34

The method of embodiment 31, wherein the agent or the combination of agents is capable of increasing the T cell ratio by at least 10%.

EXAMPLES

Example 1—Effect of Cachexia on White Blood Cell Types in C26 Cachexia Mouse Model Cachexia-inducing C26 tumor cells (see Bonetto et al. J Vis Exp. 2016 Nov. 30; (117): 10.3791/54893) were cultured in Advanced RPMI 1640 medium supplied with 5% fetal bovine serum and 1% penicillin/streptomycin (all from Thermo Fisher Scientific/Gibco) and maintained in a 5% $CO_2$, 37° C. humidified incubator (Thermo HERA CELL150 Incubator). Tumor cells with viability of >90% were used in the studies. 1×106 cells were re-suspended in 100 µl of PBS for injection and were subcutaneously injected into either the right or left flank of mice.

7 week-old BALB/c male and female mice (from Charles River Laboratories) were used for the studies. Following subcutaneous tumor inoculation, the animals were returned to cages and were monitored for the appearance of palpable tumor and cachexia development by observing and weighing body weight daily.

Body weight was measured once daily from day 8 after tumor inoculation. Tumor volume was measured once every three days from day 8 after tumor inoculation. Tumor size was calculated using the following formula: Tumor size (mm2)=L×W where, L=Length (mm); W=Width (mm). Survival time of each mouse was recorded. Blood samples were collected and white blood cells counts and neutrophil/T-cell-to-white-blood-cell ratio s were counted and analyzed by FACS at specified time points described in each example.

Blood samples from the animals were treated to deplete red blood cells (RBC), and were then subject to FACS analysis to obtain the number of white blood cells and the ratios of T cells stained with PE Anti-mouse CD3 antibody and neutrophils stained with PE anti-mouse Gr1/PE-Cy5 anti-mouse CD11b antibodies. Antibodies against mouse CD3, CD11b, CD4 and Gr1 were purchased from BD Biosciences and BioLegend. The stained cells were analyzed by flow cytometry on a Guava PCA Flow Cytometer. The percentage of each cell type was determined analysis of ratios in the respective quadrants of the FACS dot plot. White blood cells were counted on the Guava PCA Flow Cytometer using Guava ViaCount Solution from EMD Millipore.

FIG. 1 shows the results of analysis of total white blood cell population and neutrophil and T-cell-to-white-blood-cell ratios in naïve vs. cachectic mice. Cachectic (■) mice show an approximately four-fold increase in mean total white blood cell concentration relative to naïve (●) mice (FIG. 1, panel A). At the individual cell type level, this is associated mostly with an increase in neutrophils (panel B); CD3+ (T-cell) ratios decline approximately four-fold in cachectic mice (■) relative to naïve mice (●) while Gr1+/CD11b+(neutrophil) ratios increase approximately eight-fold in cachectic mice (■) relative to naïve mice (●). Thus, the data demonstrates that mice under cachexia have a significantly elevated total white blood cell count accounted for by increased Gr1+/CD11b+ neutrophils and decreased CD3+ lymphocytes ratio.

Example 2—Effect of Cytarabine, Ketorolac, and a Combination of Cytarabine and Ketorolac on Body Weight and Survival of Cachectic Mice C26 cells were prepared and cachectic mice were established, monitored, and their white blood cells analyzed according to Example 1 for all the experiments in this example.

Test compounds (Cytarabine, Ketorolac, and combinations of Cytarabine and Ketorolac) and control vehicle (PBS) were administered by subcutaneous injection. Cytarabine was obtained from Sigma-Aldrich and Ketorolac tromethamine was obtained from Tokyo Chemical Industry Co., Ltd. (TCI); both were prepared as solutions in PBS for injection.

Figure 2:
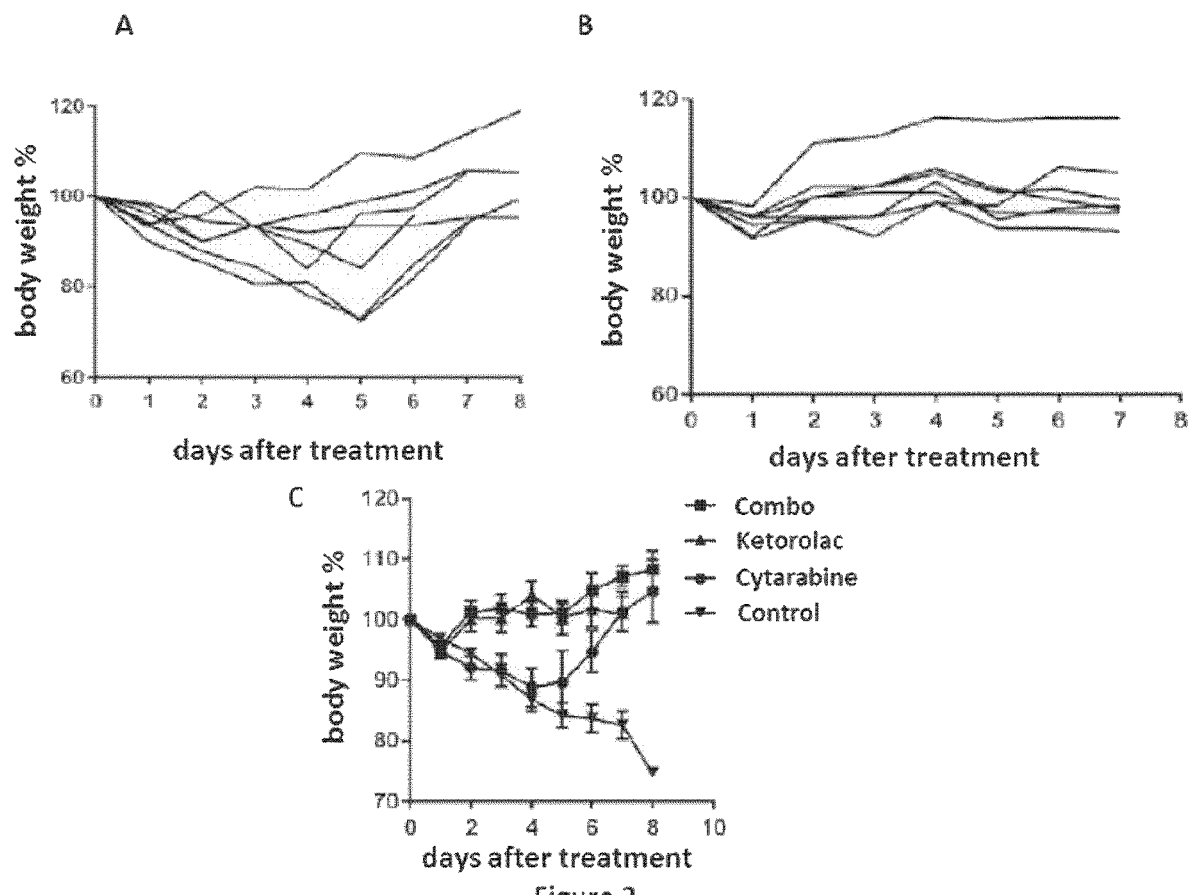
FIG. 2 demonstrates that (A) Cytarabine, (B) Ketorolac, and (C) the combination of Cytarabine and Ketorolac reverse body weight drop in cachectic mice; (A) is a graph showing individual body weights of cachectic Balb/c mice injected with C26 tumor cells post-treatment with 0.3 mg Cytarabine, (B) is a graph showing individual body weights of cachectic Balb/c mice injected with C26 tumor cells post-treatment with 0.1 mg Ketorolac, and (C) is a graph showing mean body weight±s.e.m. in cachectic Balb/c mice injected with C26 tumor cells post-treatment with 0.3 mg Cytarabine (●, n=7), 0.1 mg Ketorolac (▲, n=7), or combo (0.3 mg Cytarabine+0.1 mg Ketorolac, ■, n=7) alongside untreated mice (▼, n=7).

First, the effect of cytarabine, ketorolac, and a combination of cytarabine and ketorolac on body weight of cachectic mice was assessed. Mouse body weight was measured daily from day 7 after tumor inoculation. When mouse body weight drop exceeded 1 gram (suggesting cancer cachexia occurrence) 0.3 mg Cytarabine in PBS, 0.1 mg Ketorolac in PBS, or combination in PBS (0.3 mg Cytarabine+0.1 mg Ketorolac) was injected subcutaneously to each mouse on three consecutive days (1 cycle). FIGS. 2A and 2B show the effect of this cytarabine alone (A) and ketorolac alone (B) on body weight for individual mice (separate lines), demonstrating that, while all mice show an initial decrease in body weight after treatment, the body weight drop eventually reverses for all treated mice. FIG. 2C shows the effect of these Cytarabine (●, n=7), Ketorolac (▲, n=7), Combination (■, n=7), or no treatment (▼, n=7) regimens on body weight in cachectic mice. Untreated mice show a progressive weight loss over the entire observation period (8 days), while all of the treatment regimens eventually reverse this body weight decrease. Notably, adding ketorolac to cytarabine counteracts the transient weight loss seen on days 0-5 with cytarabine alone (●). Mice treated with the combination of cytarabine and ketorolac show the highest body weight at the end of the observation period.

Figure 3:
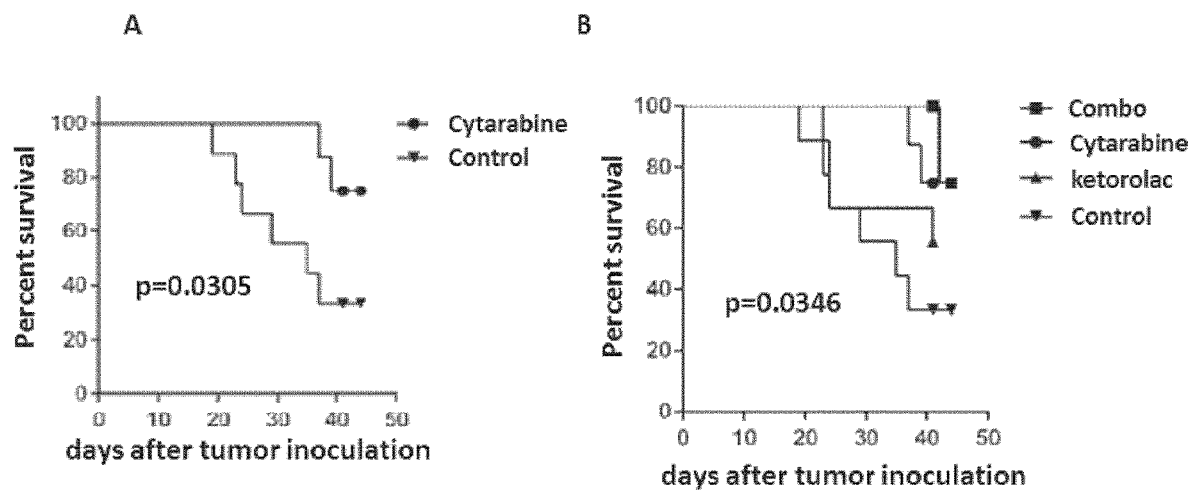
FIG. 3 demonstrates that (A) Cytarabine and (B) the combo of Cytarabine+Ketorolac prolong survival of cachectic mice; (A) is a Kaplan-Meier survival curve of cachectic Balb/c mice injected with C26 tumor cells post-two treatment cycles with 0.3 mg Cytarabine (●, n=8) or PBS control (▼, n=9), and (B) is a Kaplan-Meier survival curve of cachectic Balb/c mice injected with C26 tumor cells post-two treatment cycles with 0.3 mg Cytarabine (●, n=8), 0.1 mg Ketorolac (▲, n=9), the combo (■, n=8) or PBS control (▼, n=9).

Second, the effect of cytarabine, ketorolac, and a combination of cytarabine and ketorolac on survival of cachectic mice was assessed. FIG. 3A shows the effect of cytarabine treatment alone (●, n=8) versus PBS vehicle alone (▼, n=9) in a Kaplan-Meier survival analysis; in this case the mice were followed over a ~50 day period, treating with an additional 3-day/one-injection-per-day cycle of 0.3 mg cytarabine when body weight loss of individual mice exceeded 1 gram. The survival analysis indicated a highly significant increase in survival with mice treated with cytarabine versus vehicle alone (p=0.0305). FIG. 3B shows the effect corresponding effect of these Cytarabine (●, n=8), Ketorolac (▲, n=9), Combination (■, n=8), or PBS control (▼, n=9) regimens alongside each other in a separate Kaplan-Meier survival analysis over a ~50 day period, treating with an additional 3 day/one-injection-per-day cycle of cytarabine, ketorolac, or combination when mouse body weight decrease exceeded 1 gram for a second time. While all the treatments appear to increase survival, the combination of cytarabine and ketorolac shows the largest/most significant effect (p=0.0346 versus Ketorolac alone), followed next by cytarabine alone, and finally ketorolac alone.

Example 3—Effects of Various Cytarabine:Ketorolac Combinations on Tumor Size and White Blood Cell Types in Cachectic Mice The effect of Cytarabine:Ketorolac combinations on further phenotypes of cachectic mice was next examined. C26 cells were prepared and cachectic mice were established, monitored, and their white blood cells analyzed according to Example 1 for all the experiments in this example.

First, effect of the combination on tumor size in the C26 mouse model was assessed. Mice were treated with injections of 6:2 cytarabine:ketorolac (n=4) or vehicle (n=5) once on four consecutive days and mean tumor size±SD in mm2 was assessed. FIG. 4A shows the result of this experiment; the cytarabine:ketorolac combination had no significant effect on tumor size relative to vehicle, suggesting that the effect of the combination on cachexia in tumor bearing mice was unrelated to any anti-tumor effect of either compound.

Figure 4:
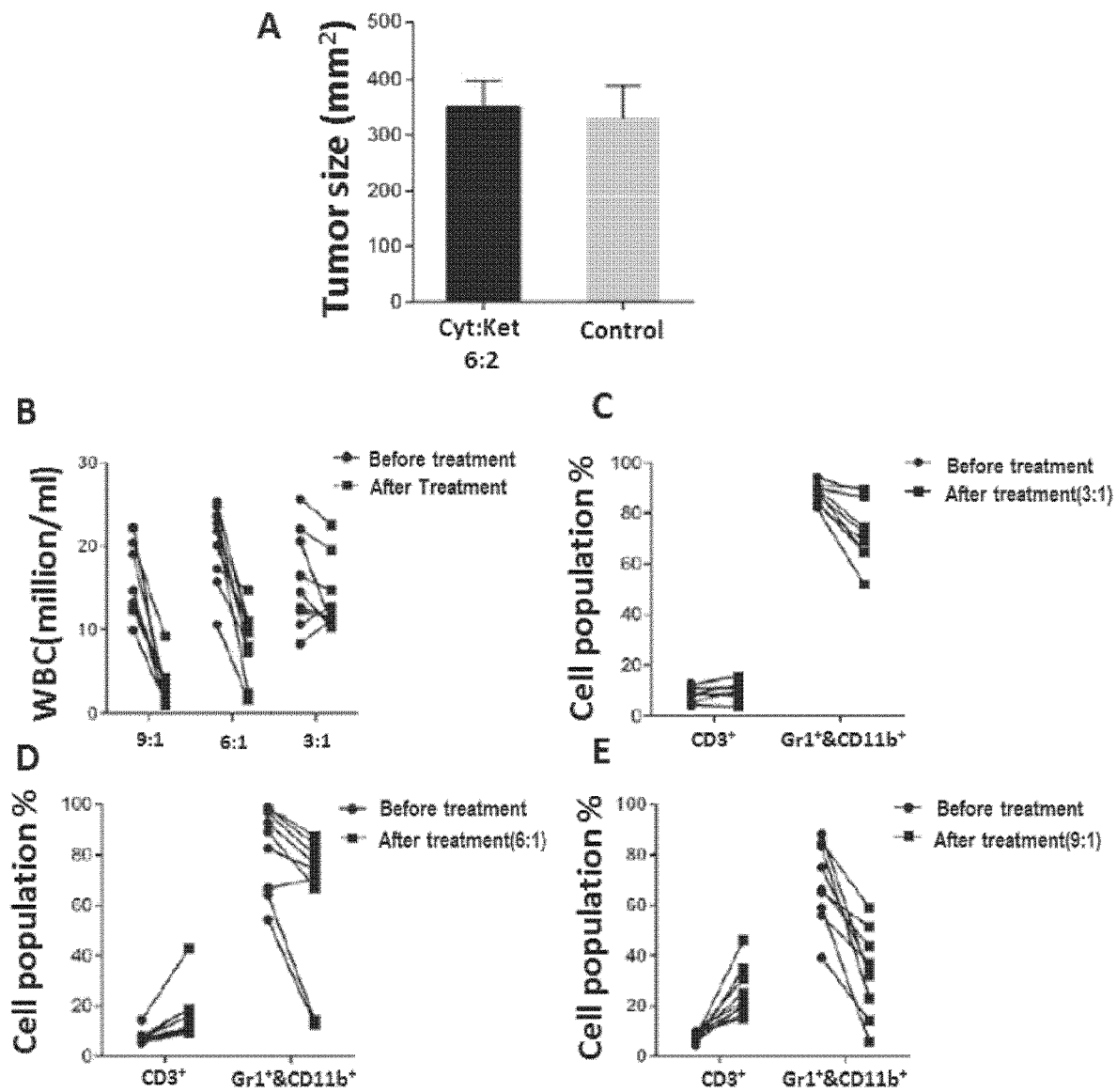
FIG. 4 demonstrates that the Cytarabine and Ketorolac combination reverses cancer cachexia in mice not by inhibition of tumor growth, but by correction of an underlying immune disorder; (A) is a graph of mean tumor size±SD in mice inoculated with C26 tumor cells treated after cachexia onset with 4 injections of cytarabine:ketorolac combination (6:2 cytarabine/ketorolac dosage ratio), (B), (C), (D), and (E) are graphs of total white blood cell populations or T-lymphocyte (CD3+) or neutrophil (Gr1+/CD11b+) ratios in mice before and after treatment with various combination ratios of Cytarabine:Ketorolac dose ratios.

Second, the effect of various ratios of cytarabine:ketorolac on white blood cell types was assessed as in Example 1 to assess whether the combination counteracted the immune disorder observed to underlie cachexia in tumor-bearing mice. Mice under cachexia were treated with cytarabine: ketorolac in PBS [3:1(n=9), 6:1(n=9), 9:1(n=9)] on 3 consecutive days (days 1-3 of the experiment). On day 1 (before treatment) and day 5 (after treatment) peripheral blood was collected and processed as in Example 5. FIG. 4 panels B, C, D, and E show graphs of total white blood cells and T-cell/neutrophil levels resulting from this experiment; lines represent individual mice. All cytarabine:ketorolac ratios show some counteracting of the abnormally high white blood cell count observed in cachectic mice (see panel B, before treatment ● versus after treatment ■), with the 9:1 ratio showing the strongest effect, followed by the 6:1 ratio, and then the 3:1 ratio. All cytarabine:ketorolac ratios also show some counteracting of the abnormally high (Gr1+/CD11b+) neutrophil levels [see panels C (3:1), D (6:1) and E (9:1)], with the 9:1 ratio again showing the strongest effect, followed by the 6:1 ratio, and then the 3:1 ratio. Overall, the data suggest that cytarabine:ketorolac combinations counteract the immune disorder observed in cachectic mice. All cytarabine:ketorolac ratios also show some counteracting of the abnormally low (CD3+) T-cell levels [see panels C (3:1), D (6:1) and E (9:1)], again with the 9:1 ratio again showing the strongest effect, followed by the 6:1 ratio and then the 3:1 ratio.

Figure 5:
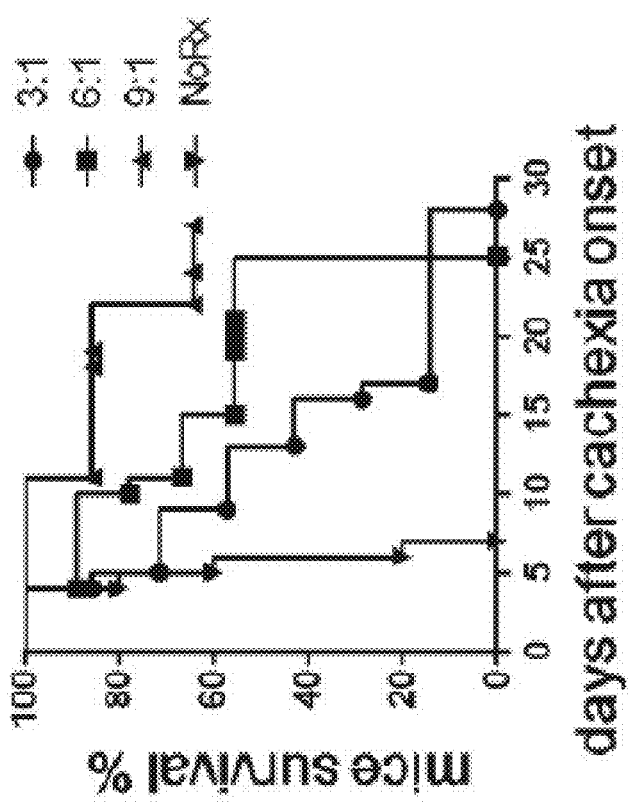
FIG. 5 demonstrates that higher ratios of Cytarabine to Ketorolac further improve survival of cachectic mice.

Third, the effect of various ratios of cytarabine:ketorolac on survival of cachectic mice was assessed to determine the optimal cytarabine:ketorolac ratio for cachexia treatment. Mice under cachexia were treated with three fixed dose combination regimens: 3:1(n=7), 6:1(n=9) and 9:1(n=7). At least three cycles of 3-day/one-injection-per-day treatment were given. Mice were observed over ~30 days and a Kaplan-Meier survival analysis was performed. The results of the Kaplan-Meier survival analysis are shown in FIG. 5. The effectiveness of the combinations on survival showed dose-dependence on cytarabine ratio: the 9:1 ratio of cytarabine:ketorolac (▼) showed the largest effect on survival, followed next by the 6:1 ratio (■) and the 3:1 ratio (●).

Figure 6:
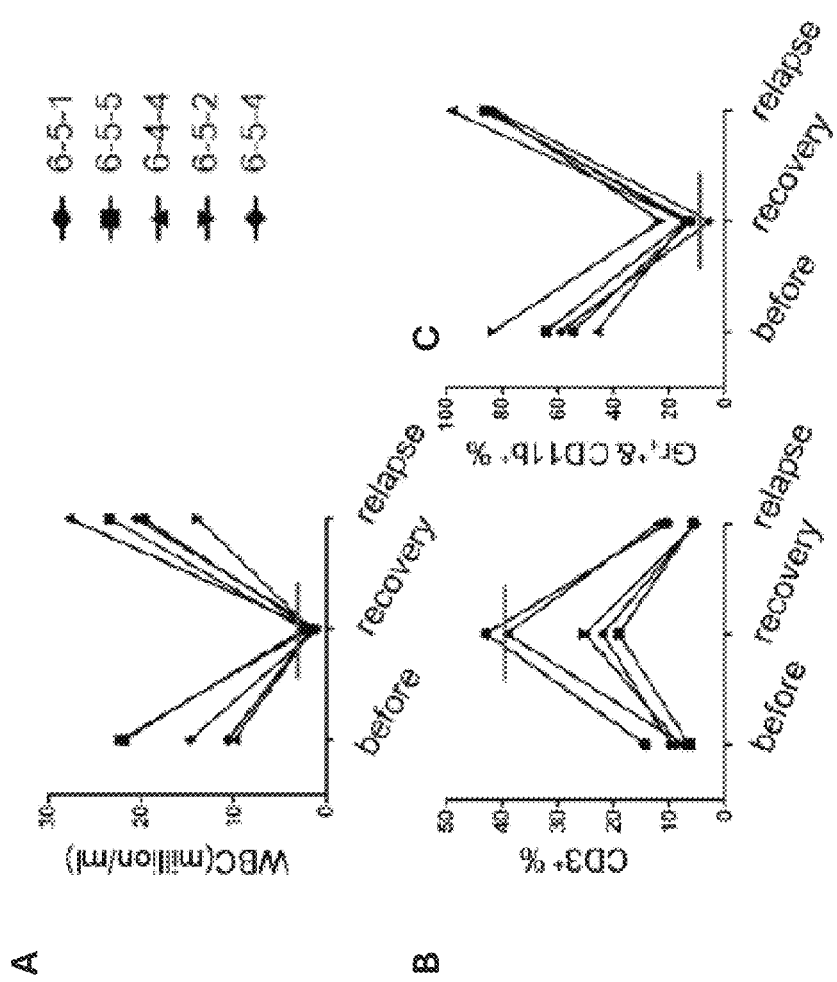
FIG. 6 demonstrates that white blood cell response to the Cytarabine/Ketorolac combination correlates with its efficacy on cancer cachexia; (A), (B) and (C) are graphs depicting total white blood cell population (A), T-cell-to-white-blood-cell ratio (B), or neutrophil-to-white-blood-cell ratio (C) in individual mice treated with 6:1(●,■), or 9:1(▲,▼,♦) Cytarabine:Ketorolac before combination treatment, after combination treatment, and upon relapse of cachexia alongside the corresponding levels in mice without cachexia (the corresponding level in mice without cachexia is represented by the reference line).

Finally, the correlation of white blood cell ratios to cachexia onset, recovery, and relapse was determined to assess to what degree these measures are useful biomarkers of cachexia. Mice under cachexia were treated with a cytarabine:ketorolac combination [6:1 or 9:1] on day 1, day 2 and day 3. On day 1 (before treatment), day 5 (after treatment when mice body weight has returned to normal level) and on the day (may be different for each individual mouse) when mice body weight begin to drop again peripheral blood was collected and processed as in Example 5. The results of this experiment are shown in FIG. 6 panels A, B, and C, where individual lines represent individual mice, the horizontal bar represents levels of cells in mice without cachexia, ●/■ represent mice treated with 6:1 ratio, and ▲/▼/♦ represent mice treated with the 9:1 ratio. Consistent with the total white blood cell population and T-cell/neutrophil-to-white-blood-cell ratios being biomarkers of cancer cachexia, all 3 phenotypes show treatment/recovery-dependent reversions to approximately normal levels (horizontal bar), and cachexia onset/relapse-dependent deviations away from normal levels.

Example 4—Effect of Repeated Treatment Cycles of Cytarabine/Ketorolac Combinations on Cancer Cachexia An experiment was performed to assess whether repeated cycles of Cytarabine/Ketorolac combinations are effective in counteracting relapsed cachexia. C26 cells were prepared and cachectic mice were established, treated, monitored, and their white blood cells analyzed according to Examples 1 and 2 for all the experiments in this example.

Figure 7:
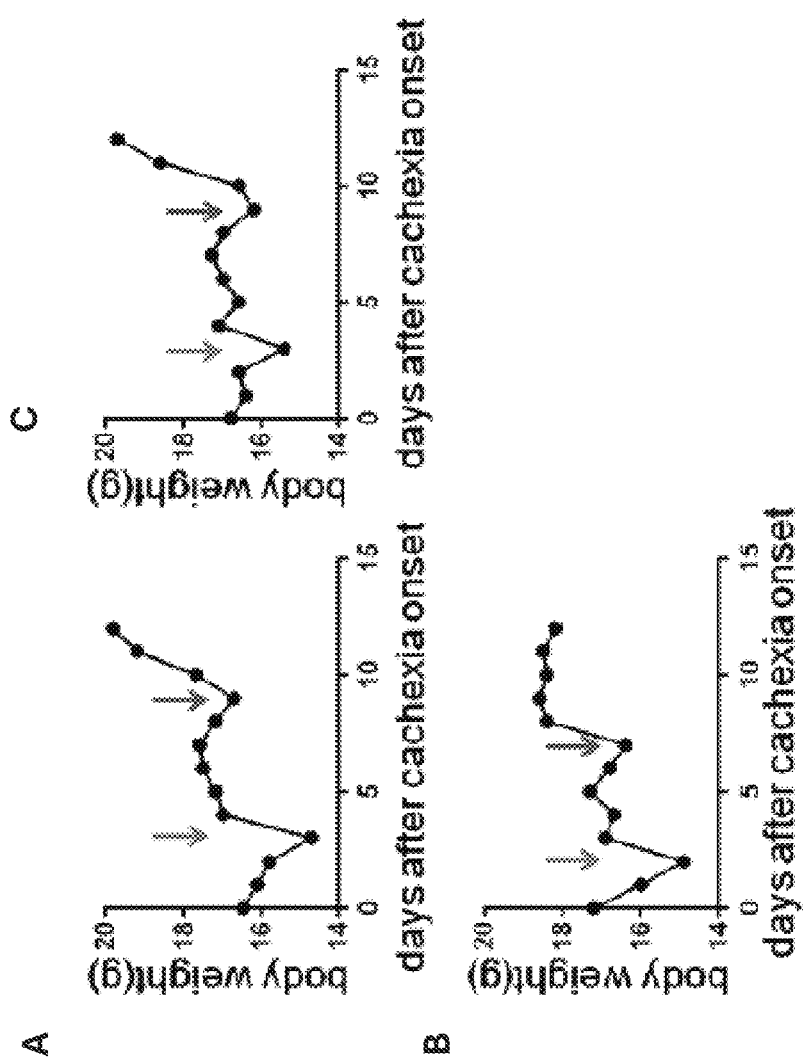
FIG. 7 demonstrates that the cytarabine:ketorolac treatment can be used multiple times over the course of cancer treatment to counteract cachexia. Panels (A), (B), and (C) display graphs of body weights of individual mice, with times of Cytarabine/Ketorolac treatment delineated by arrows.

After a first cycle of treatment (three injections of 3:1 dosage on three consecutive days) mouse body weight was followed daily. When cachexia relapsed after the first cycle of treatment a second cycle of treatment was given. FIG. 7 panels A, B, and C show graphs of body weight change of 3 representative mice during the treatment course with time of treatment administration shown by arrows. After the first round of treatment (leftmost arrow in each panel), all three mice show increases in body weight for multiple days; all three mice subsequently show body weight declines consistent with relapse of cachexia. A second round of treatment (rightmost arrow in each panel) counteracts this decline and body weight of all three mice again increases. Overall, the data suggests that cytarabine/ketorolac injections are effective when administered multiple times to the same subject to treat the chronic disease, and intermittent cachexia treatment may be employed in combination with cancer therapy in an alternative fashion.

Example 5—Effect of (R)-Ketorolac on Body Weight and Survival in Cachectic Mice

An experiment was performed to assess whether enantiomerically pure forms of Ketorolac have increased efficacy. C26 cells were prepared and cachectic mice were established, treated, monitored, and their white blood cells analyzed according to Examples 1 and 2 for all the experiments in this example. ≥95% enantiomerically pure (R)-Ketorolac was obtained from Sigma-Aldrich.

Figure 8:
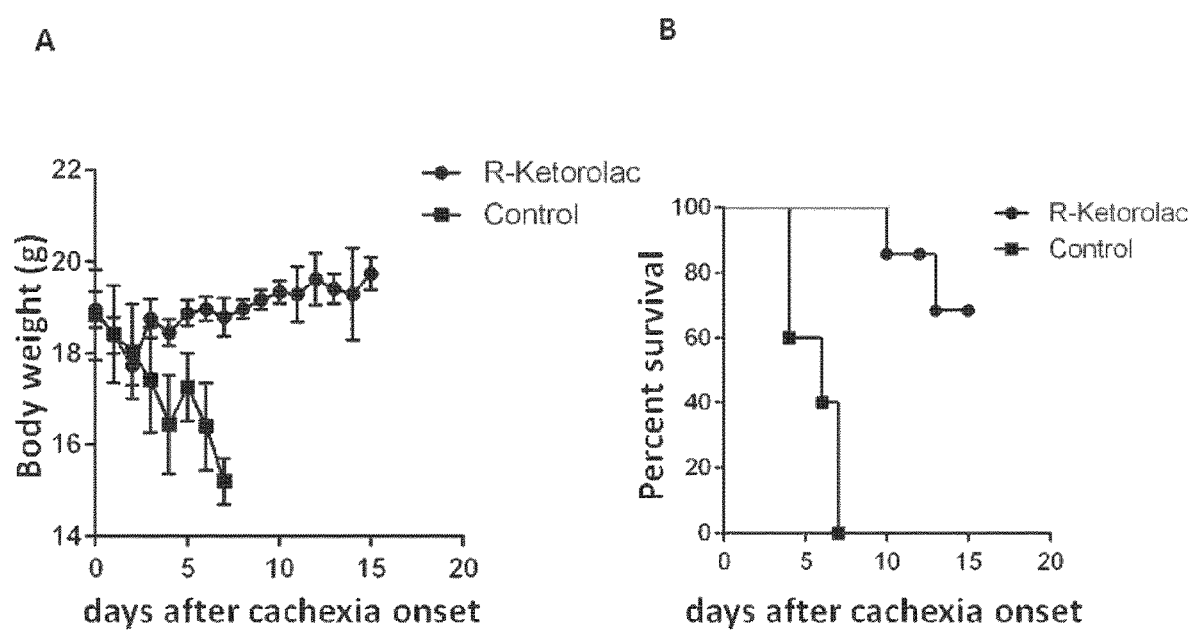
FIG. 8 demonstrates that (R)-Ketorolac alone can reverse body weight drop and prolong survival of cachectic mice. (A) is a graph showing mean body weight±s.e.m. in cachectic mice treated with 0.05 mg (R)-ketorolac (●, n=5) or PBS control (■, n=5). (B) is a Kaplan-Meier survival curve of cachectic mice treated with 0.05 mg (R)-ketorolac (●, n=7) or PBS control (■, n=5).

First, the effect of (R)-ketorolac on body weight of cachectic mice was assessed. Mouse body weight was measured daily from day 7 after tumor inoculation. When mouse body weight drop exceeded 1 gram (suggesting cancer cachexia occurrence), 0.05 mg (R)-ketorolac in PBS was given orally to each mouse on three consecutive days (1 cycle). FIG. 8A shows the result of 6 days/2 cycles of (R)-ketorolac treatment on body weight of (n=5) cachectic mice. Compared to cachectic mice treated with PBS (n=5), mice treated with (R)-ketorolac regained body weight after initiation of the treatment and maintained stabilized body weight during the treatment. This result was unexpected, as (S)-ketorolac is generally considered the active enantiomer of ketorolac (see e.g., Handley et al. J Clin Pharmacol. 1998 February; 38(2 Suppl):255-35S).

Second, the effect (R)-ketorolac alone on survival of cachectic mice was assessed. FIG. 8B shows the effect of (R)-ketorolac treatment alone (●, n=7) versus PBS vehicle alone (■, n=5) in a Kaplan-Meier survival analysis; in this case the mice were followed over a 40 day period, treating with two cycles of daily oral administration of (R)-ketorolac when body weight loss of individual mice exceeded 1 gram. (R)-ketorolac showed significant efficacy as a single agent increasing the survival of cachectic mice (p=0.0005).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for treating cachexia, consisting of administering to a subject in need thereof an effective amount of an agent according to formula V or a pharmaceutically acceptable salt, solvate, hydrate, or clathrate thereof

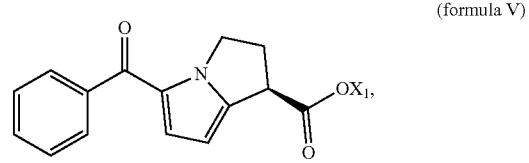

(formula V)

wherein:
X1 is selected from the group consisting of a H, a straight-chain or branched saturated or unsaturated C1-C20 aliphatic group optionally substituted with a C6-C10 aryl group, —NHC6H5, —NHC6H5OCH3, —NHCH2C6H5, —NHCH26H4OCH3, —NHCH2COOCH3, —NHCH2CH2COOC2H5, —NHCH2(CH2)2CH3, —NHC6H10, —NHCH2CH2CH3, —NHCH(CH3)2, —NH(CH2)3OCH3, —NHCH2CH=CH2, optionally substituted talosyl, optionally substituted galactosyl, optionally substituted idosyl, optionally substituted glucosyl, optionally substituted mannosyl, optionally substituted glucosyl, optionally substituted altrosyl, optionally substituted allosyl, optionally substituted alkylpiperidinyl, optionally substituted piperizinyl, optionally substituted alkylpiperazinyl, optionally substituted morpholinyl, and optionally substituted alkylmorpholinyl.

2. The method of claim 1, wherein the agent according to formula V is (R)-ketorolac.

3. The method of claim 2, wherein the method at least one of:
(a) effectively decreases the white blood cell amount of the subject by at least about 10%;
(b) effectively decreases a neutrophil-to-white-blood-cell ratio of the subject by at least about 10%;
(c) effectively increases a T-cell-to-white-blood-cell ratio of the subject by at least about 10%; and
(d) effectively increases the body weight of the subject by at least about 10%.

* * * * *